US011963716B2

United States Patent
Beale et al.

(10) Patent No.: US 11,963,716 B2
(45) Date of Patent: *Apr. 23, 2024

(54) APPARATUS AND METHOD FOR THE TREATMENT OF DERMATOLOGICAL DISEASES OR CONDITIONS

(71) Applicant: Emblation Limited, Alloa (GB)

(72) Inventors: Gary Beale, Stirling (GB); Eamon McErlean, Alloa (GB)

(73) Assignee: EMBLATION LIMITED, Alloa (GB)

( * ) Notice: Subject to any disclaimer, the term of this patent is extended or adjusted under 35 U.S.C. 154(b) by 57 days.

This patent is subject to a terminal disclaimer.

(21) Appl. No.: 15/213,946

(22) Filed: Jul. 19, 2016

(65) Prior Publication Data

US 2016/0324577 A1 Nov. 10, 2016

Related U.S. Application Data

(63) Continuation-in-part of application No. 13/183,759, filed on Jul. 15, 2011, now Pat. No. 9,662,510.

(Continued)

(51) Int. Cl.
| | |
|---|---|
| A61B 18/18 | (2006.01) |
| A61N 5/02 | (2006.01) |
| A61N 5/04 | (2006.01) |
| A61N 5/06 | (2006.01) |
| A61B 18/00 | (2006.01) |

(52) U.S. Cl.
CPC .......... *A61B 18/1815* (2013.01); *A61N 5/025* (2013.01); *A61N 5/04* (2013.01); *A61N 5/0624* (2013.01); *A61B 2018/00452* (2013.01); *A61B 2018/00577* (2013.01); *A61B 2018/00589* (2013.01); *A61B 2018/00595* (2013.01); *A61N 5/0616* (2013.01)

(58) Field of Classification Search
CPC . A61B 18/18; A61B 18/1815; A61B 2018/18; A61B 2018/1807; A61B 2018/1815; A61B 2018/1823
See application file for complete search history.

(56) References Cited

U.S. PATENT DOCUMENTS

| | | | |
|---|---|---|---|
| 4,149,170 | A | 4/1979 | Campbell et al. |
| 4,517,975 | A | 5/1985 | Garito et al. |

(Continued)

FOREIGN PATENT DOCUMENTS

| | | |
|---|---|---|
| CN | 1277879 | 12/2000 |
| CN | 102905639 | 1/2013 |

(Continued)

OTHER PUBLICATIONS

Li Hx, Zhu Wy, Xia My. Detection with the polymerase chain reaction of human papillomavirus DNA in condylomata acuminata treated with CO2 laser and microwave. Int J Dermatol 1995;34:209-211. (Year: 1995).*

(Continued)

*Primary Examiner* — Joseph A Stoklosa
*Assistant Examiner* — Adam J Avigan
(74) *Attorney, Agent, or Firm* — Sheridan Ross P.C.

(57) ABSTRACT

Methods and apparatus for the treatment of dermatological conditions, including, for example, viral infections, microbial infections, cancers, dermatological conditions and particularly infections of the skin caused by human papillomavirus (HPV).

13 Claims, 25 Drawing Sheets

Related U.S. Application Data

(60) Provisional application No. 61/365,447, filed on Jul. 19, 2010.

(56) References Cited

U.S. PATENT DOCUMENTS

| | | | |
|---|---|---|---|
| 4,914,717 | A | 4/1990 | Gibbon |
| 5,091,707 | A | 2/1992 | Wollmerschauser et al. |
| 5,195,965 | A * | 3/1993 | Shantha .................. A61F 7/123 |
| | | | 604/114 |
| 5,272,301 | A * | 12/1993 | Finger ................ A61B 18/1815 |
| | | | 219/696 |
| 5,507,791 | A | 4/1996 | Sit'ko |
| 5,649,973 | A | 7/1997 | Tierney et al. |
| 5,683,386 | A | 11/1997 | Ellman et al. |
| 5,879,379 | A | 3/1999 | Mason et al. |
| 5,993,480 | A | 11/1999 | Burrows |
| 6,047,216 | A | 4/2000 | Carl et al. |
| 6,104,959 | A | 8/2000 | Spertell |
| 6,710,673 | B1 | 3/2004 | Jokerst |
| 7,052,283 | B2 | 5/2006 | Pixley et al. |
| 7,211,411 | B2 | 5/2007 | Neefe et al. |
| 7,292,893 | B2 | 11/2007 | Hoenig et al. |
| 7,981,112 | B1 | 7/2011 | Neev |
| 9,498,284 | B2 | 11/2016 | McErlean et al. |
| 9,543,061 | B2 | 1/2017 | McErlean et al. |
| 9,662,510 | B2 | 5/2017 | Beale et al. |
| 11,083,521 | B2 | 8/2021 | McErlean et al. |
| 2001/0050605 | A1 | 12/2001 | Suggiura et al. |
| 2003/0012830 | A1 | 1/2003 | Small |
| 2003/0225441 | A1 * | 12/2003 | Boynton .................... A61F 7/00 |
| | | | 607/104 |
| 2004/0202663 | A1 | 10/2004 | Hu et al. |
| 2005/0251231 | A1 | 11/2005 | Goldberg |
| 2006/0020312 | A1 * | 1/2006 | Eggers ................... A61B 18/04 |
| | | | 607/103 |
| 2006/0235286 | A1 | 10/2006 | Stone et al. |
| 2006/0265034 | A1 | 11/2006 | Aknine et al. |
| 2008/0149100 | A1 | 6/2008 | Van Holst et al. |
| 2008/0183164 | A1 | 7/2008 | Elkins et al. |
| 2008/0294073 | A1 | 11/2008 | Barthe et al. |
| 2008/0319517 | A1 | 12/2008 | Cumbie |
| 2010/0010480 | A1 | 1/2010 | Mehta et al. |
| 2010/0036369 | A1 | 2/2010 | Hancock |
| 2010/0114086 | A1 * | 5/2010 | Deem .................... A61B 18/18 |
| | | | 606/33 |
| 2010/0211059 | A1 | 8/2010 | Deem et al. |
| 2012/0016356 | A1 | 1/2012 | Beale et al. |
| 2012/0203218 | A1 | 8/2012 | Bonn |
| 2013/0178383 | A1 | 7/2013 | Spetzler et al. |
| 2013/0190750 | A1 | 7/2013 | Behnke et al. |
| 2013/0282084 | A1 | 10/2013 | Mathur et al. |
| 2014/0066837 | A1 | 3/2014 | Moy |
| 2014/0249601 | A1 | 9/2014 | Bachinski et al. |
| 2014/0356397 | A1 | 12/2014 | Akle et al. |
| 2015/0024961 | A1 | 1/2015 | Klass et al. |
| 2015/0080875 | A1 | 3/2015 | Kasprzyk et al. |
| 2016/0022976 | A1 | 1/2016 | Peyman |
| 2018/0036551 | A1 | 2/2018 | McErlean et al. |
| 2018/0280715 | A1 | 10/2018 | McErlean et al. |
| 2019/0069949 | A1 | 3/2019 | Vrba et al. |
| 2019/0255348 | A1 | 8/2019 | Beale et al. |
| 2019/0274758 | A1 | 9/2019 | Beale et al. |
| 2020/0353278 | A1 | 11/2020 | McErlean et al. |

FOREIGN PATENT DOCUMENTS

| | | |
|---|---|---|
| EP | 2485326 | 8/2012 |
| JP | 2010-507403 | 3/2010 |
| JP | 2012-506300 | 3/2012 |
| JP | 2012-508062 | 4/2012 |
| JP | 2013-523346 | 6/2013 |
| JP | 2013-525075 | 6/2013 |
| JP | 2014-531935 | 12/2014 |
| JP | 2015-037587 | 2/2015 |
| JP | 2016-010729 | 1/2016 |
| JP | 2016-501575 | 1/2016 |
| WO | WO 91/03207 | 3/1991 |
| WO | WO 93/22977 | 11/1993 |
| WO | WO 98/49933 | 11/1998 |

OTHER PUBLICATIONS

Choi et al. "Short-Term Heat Exposure Inhibits Inflammation by Abrogating Recruitment of and Nuclear Factor-κB Activation in Neutrophils Exposed to Chemotactic Cytokines." The American Journal of Pathology, 2008, vol. 172(2), pp. 367-377.

De Pomerai et al. "Growth and maturation of the nematode Caenorhabditis elegans following exposure to weak microwave fields." Enzyme and Microbial Technology, 2002, vol. 30(1), pp. 73-79.

Fausch et al. "Human Papillomavirus Can Escape Immune Recognition through Langerhans Cell Phosphoinositide 3-Kinase Activation." The Journal of Immunology, 2005, vol. 174(11), pp. 7172-7178.

Gao et al. "Non-ablative controlled local hyperthermia for common warts." Chinese Medical Journal, 2009, vol. 122(17), pp. 2061-2063.

Kashima et al. "Polymerase chain reaction identification of human papillomavirus DNA in CO2 laser plume from recurrent respiratory papillomatosis." Otolaryngol Head Neck Surgery, 1991, vol. 104(2), pp. 191-195.

Li et al. "Detection with the Polymerase Chain Reaction of Human Papillomavirus DNA in Condylomata Acuminata Treated with CO2 laser and Microwave." International Journal of Dermatology, 1995, vol. 34(3), pp. 209-211.

Lipke "An Armamentarium of Wart Treatments," Clinical Medicine & Research, 2006, vol. 4(4), pp. 273-293.

Ogura et al. "Microwave hyperthermia treatment increases heat shock proteins in human skeletal muscle," British Journal of Sports Medicine, 2007, vol. 41, pp. 453-455.

Skitzki et al. "Hyperthermia as an immunotherapy strategy for cancer." Current Opinion in Investigational Drugs, Jun. 2009, vol. 10(6), pp. 550-558.

Tonomura et al. "Effects of Heat Stimulation via Microwave Applicator on Cartilage Matrix Gene and HSP70 Expression in the Rabbit Knee Joint." Journal of Orthopaedic Research, 2008, vol. 26(1), pp. 34-41.

Official Action for U.S. Appl. No. 13/183,759, dated Feb. 14, 2014, 13 pages.

Final Action for U.S. Appl. No. 13/183,759, dated Nov. 3, 2014, 16 pages.

Official Action for U.S. Appl. No. 13/183,759, dated Oct. 22, 2015, 15 pages.

Final Action for U.S. Appl. No. 13/183,759, dated Jun. 3, 2016, 17 pages.

Notice of Allowance for U.S. Appl. No. 13/183,759, dated Feb. 14, 2017, 14 pages.

"Phenol," HPA Compendium of Chemical Hazards, 2011, Version 4, 32 pages.

Bevans et al. "A comparison of electrosurgery and sharp debridement in the treatment of chronic neurovascular, neurofibrous and hard corns. A pragmatic randomised controlled trial," The Foot, Mar. 2010, vol. 20, No. 1, pp. 12-17.

Cavaliere "Treatment of Porokeratosis Plantaris Discreta," The Podiatry Institute, (Predilection and Clinical Assessment), 1993, pp. 145-149 [retrieved online from: www.poodiatryinstitute.com/pdfs/update_1993/1993_28.pdf].

Chapeskie, "Ingrown Toenail or overgrown toe skin?" Canadian Family Physician, 2008, vol. 54, No. 11, pp. 1561-1562.

Clayton et al., Patty's Industrial Hygiene and Toxicology, 3rd Edition, J Wiley and Sons, New York, 1982, p. 2583.

Coughlin "Common Causes of Pain in the Forefoot in Adults," The Journal of Bone & Joint Surgery (Br), Aug. 2000, vol. 82-B, No. 6, pp. 781-790.

Koltaj "Er:YAG Laser Treatment of Intractable Plantar Keratosis (IPK)," Journal of the Laser and Health Academy, May 2013, vol.

(56) References Cited

OTHER PUBLICATIONS

2013, No. 1, pp. 32-35 [retrieved online from: https://www.laserandhealthacademy.com/media/objave/academy/priponke/32_35 koltaj intractable_plantar_keratosis jlaha_2013_1.pdf] .

Parker et al. "Specifying a Ferrite for EMI Suppression," Conformity, Jun. 2008, pp. 50-59.

Smith et al. "Microwave thermal balloon angioplasty in the normal rabbit," American Heart Journal, Jun. 1992, vol. 123, No. 6, pp. 1516-1521.

* cited by examiner

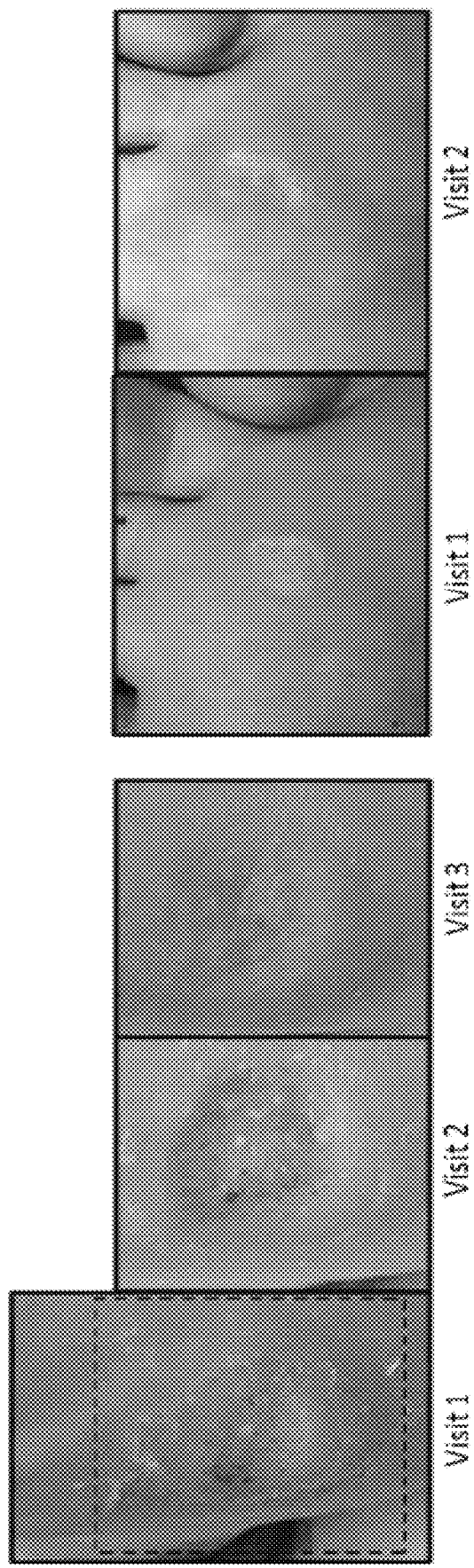

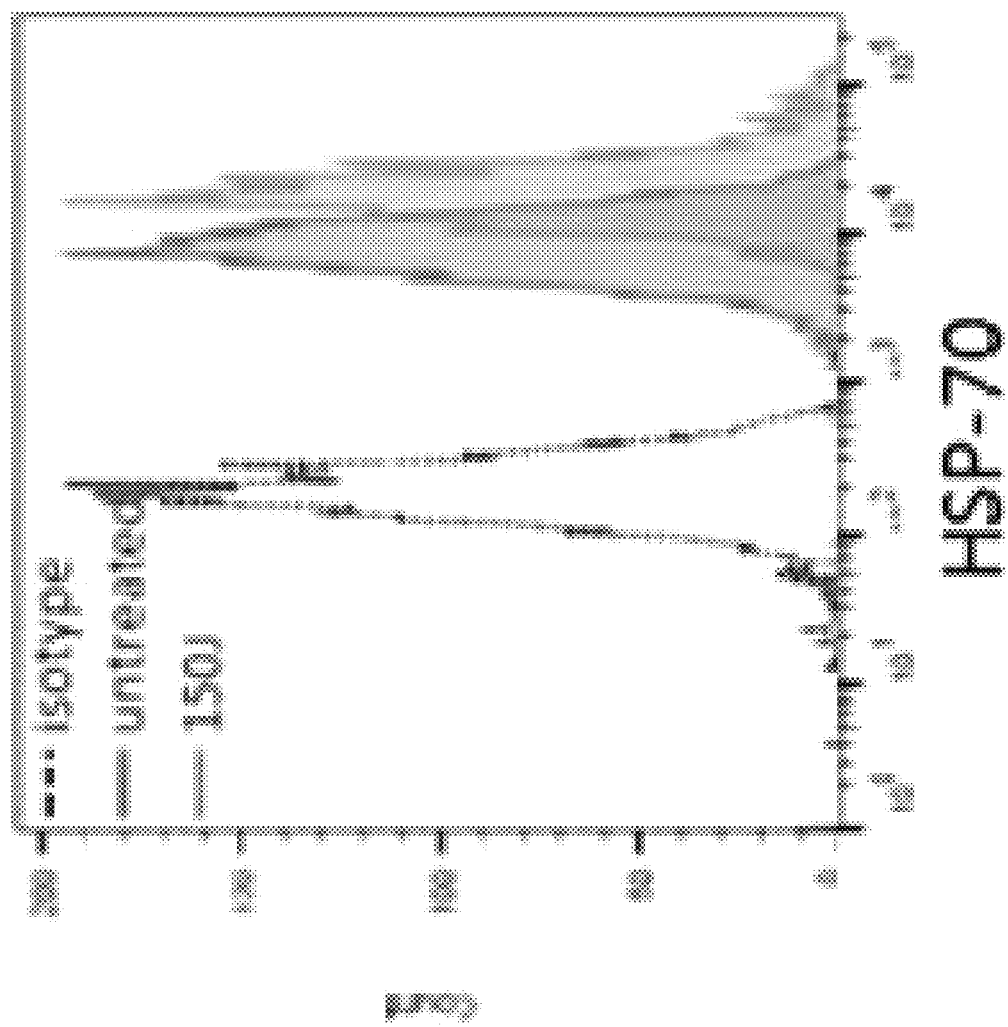

APPARATUS AND METHOD FOR THE TREATMENT OF DERMATOLOGICAL DISEASES OR CONDITIONS

FIELD OF THE INVENTION

The present invention provides methods and apparatus for the treatment of dermatological diseases and/or conditions, including, for example, viral infections, microbial infections, cancers, dermatological conditions and particularly infections of the skin caused or contributed to by human papillomavirus (HPV)

BACKGROUND

The HPV virus is highly contagious and is typically treated using cryotherapy, salicylic acid, laser surgery silver nitrite, RF ablation, homeopathy, hypnosis, adhesive tape occlusion and various other treatments none of which are currently satisfactory in providing a rapid, reliable, repeatable and efficacious treatment. An extensive review of all current HPV treatments has been compiled by Lipke (*Clin Med Res;* 4: 273-93. (2006)) which highlighted that as of 2006 there has been no reported clinical application of microwave treatment.

Some therapies rely upon ablation or removal of HPV infected tissue, however these methods do not treat the underlying HPV infection and the virus may remain in a latent state which risks further recurrence of the disease. A Quiescent HPV infection can exist within the body for an extended duration (in some case years) before reoccurrence takes place. HPV Lesions such as warts or verrucae are undetected by the immune system preventing their removal until such time as the immune system identifies the virus. Once this occurs the papilloma caused by the virus has been known to spontaneously resolve.

A few HPV strains (HPV5, 8, 16, 18, 30, 31, 33, 35, 39, 40) are known to be malignant with some strains causing cervical cancer which if diagnosed early is treatable.

It is known that microwave hyperthermia (elevated heating) can be used to ablate tissue and cells and this has also been shown to damage the HPV virus. Ii et al. (*Int J Dermatol* 1995:34:209-211. (1995)) teaches that in vitro exposure of excised condylomata acuminate to microwave energy produces more HPV DNA damage than exposure to CO2 laser.

A number of treatments have attempted to use heat to elevate the temperature of HPV infected tissue. Heat denatures the virus by destroying the shell of the viral particles exposing the antigenic site within the viral structure. The denatured viral particles are collected by sub dermal macrophages and lymphocytes which lead to the immune system producing antibodies to target remaining viruses thus eliminating the systemic HPV infection for that particular strain of the virus.

The deposition of energy and thus treatment efficacy using heat is significantly affected by the delivery modality chosen e.g. $CO_2$ laser targets the superficial surface tissue layers and does not penetrate deeply. Likewise RF ablation is not focused and relies upon grounding paths through the body. Kashima et al. (*Otolaryngol Head Neck Surg* 104(2):191-5 (1991)) teach that these methods also carry the risk of infecting those applying the treatment as the smoke plume ejected by the high energy vaporization of tissue is known to carry HPV virus particles which can infect the respiratory tract.

Microwave radiation can easily penetrate deeply within the epidermal layers to the dermis. The HPV virus is known to reside in the stratum basale and is replicated in the stratum spinosum and stratum granulosum. In very rare cases recurrent HPV infections have had virus particles found within the dermis. Microwave radiation can heat deeper layers resulting in a superior deposition of energy within the lesion. Additionally microwave energy causes heating and gradual desiccation of tissue without generating the harmful smoke plume associated with high energy vaporization.

It is established that heat shock proteins (HSP) are produced in response to various tissue stresses or damage resulting from physical or environmental influences. Heat shock proteins are a class of functionally related proteins whose expression is increased when cells are exposed to elevated temperatures or other stress. It has been suggested that the heat shock proteins may protect the cells from other stressors or against further damage. Heat shock proteins are also involved in antigen presentation, steroid receptor function, intracellular trafficking, nuclear receptor binding, and apoptosis. Typically exposure of cells to a heat shock temperature of 42 degrees C. results in transient activation of heat shock factor (HSF). The DNA-binding activity increases, plateaus, and dissipates, during which the intracellular levels of heat shock protein increase. Heat shock proteins can perform specific functions, for example extracellular and membrane bound heat-shock proteins, especially HSP70 are involved in binding antigens and presenting them to the immune system.

The upregulation of the heat shock proteins is a principle part of the heat shock response and is primarily induced by the heat shock factor. Cellular stresses, such as increased temperature, can cause proteins in the cell to denature. Heat shock proteins bind to the denatured proteins and dissociate from HSF to form trimers and translocate to the cell nucleus to activate transcription resulting in the production of new heat shock proteins which bind to more denatured cells.

In research into the physiological heating effects of electromagnetic fields, high frequency microwave energy (existing between 500 MHz to 200 GHz) has been reported to thermally produce elevated levels of specific heat shock proteins in tissue for example Ogura, *British Journal of Sports Medicine* 41, 453-455. (2007)) teaches that HSP90, HSP72, HSP27 levels are significantly higher in heated vastus lateralis muscle compared with unheated controls. Tonomura et al. (*J Orthop Res.* 26(1):34-41. (2008)) teach that in vivo HSP70 expression in rabbit cartilage increases with the application of moderate levels of microwave power (20-40 W). Additionally de Pomerai et al. (*Enzyme and Microbial Technology* 30, 73-79 (2002)) teaches that prolonged exposure to weak microwave fields (750-1000 MHz, 0.5 w) at 25° C. induces a heat-shock response in transgenic *C. elegans* strains carrying HSP16 reporter genes.

In other unrelated research, U.S. Pat. No. 7,211,411 teaches that HPV can be treated using vaccines containing heat shock proteins as immunologic adjuvants (HSPs). These vaccines fuse specific heat shock protein elements (e.g. HSP60, HSP65. HSP70) with immunostimulatory or antigenic HPV fragments, (e.g. the HPV E7 protein) to invoke a potent immune response to the HPV virus however the vaccine is limited to the strain of the virus used of which more than 100 have been identified. It has been speculated that HSPs may also be involved in binding with protein fragments from dead malignant cells and highlighting them to the immune system thus boosting the effectiveness of the vaccine, e.g Oncophage (Antigenics Inc, Lexington, MA).

Heat shock proteins not only carry antigens but can also induce naturation of dendritic cells, resulting in a more efficient antigen presentation. It is known that hyperthermia can promote the activation of the Langerhans cells. Langerhans cells are the dendritic cells of the skin which continuously monitor the extracellular matrix of the skin and capture, uptake and process antigens to become antigen presenting cells (APC's). Particles and antigens are carried to draining lymph nodes for presentation to T lymphocytes. T cells release chemokines which cause the skin to be infiltrated by neutrophils, resulting in a swelling response which has been observed by Gao et al. (*Chin Med J* (*Engl*), 122(17):2061-3 (2009)) to occur before resolution of a HPV infection.

Hyperthermia also increases the expression of key adhesion molecules in secondary lymphoid tissues. Additionally hyperthermia can also act directly on lymphocytes to improve their adhesive properties. Hyperthermia increases the intravascular display of homeostatic chemokines, and certain inflammatory chemokines which have been proposed by Skitzki et al. (*Curr Opin Investig Drugs*, 10(6):550-8 (2009)) to be classical HSP's based on their regulation by HSP transcription factors It has been observed by Fausch et al. (*J. Immunol.* 174:7171-7178 (2005)) that HPV can escape immune system recognition through Langerhans cell Phosphoinositide 3-Kinase activation (PI3-K). The inhibition of PI3-K allows Langerhans cells to initiate a potent HPV-specific response. Mild hyperthermia involving temperature spiking to mimic fever has been shown by Choi et al, (*Am J Pathol* 172:367-777, 2008) to down-regulate the PI3-K/Akt signalling pathway. Inhibition of PI3-K/Akt by heat also has an inhibitory effect on neutrophil migration which downregulates the inflammatory response.

It is hereby hypothesized that the application of mild localized hyperthermia of a pulsed nature may inhibit PI3-K helping the immune system in identifying the underlying HPV infection promoting Langerhans cells and heat shock proteins to identify and present the HPV virus to the immune system causing a localized inflammatory response followed by eradication.

The emerging understanding is that hyperthermia treatments work at multiple levels via complex complementary mechanisms involving a variety of signalling and trafficking molecules.

SUMMARY

It is proposed here that microwave energy may be employed as a tri-action (heat shock promoting, immunostimulatory, viral denaturing and tissue coagulation) treatment for diseases and/or conditions caused or contributed to by human papilloma virus (HPV), malignant conditions (including those with an HPV aetiology) and/or a range of dermatological conditions including those in which tissue (for example skin) is infected with one or more microbial (for example viral) pathogen(s).

The microwave treatment mechanism may thermally instigate the production of heat shock factor HSF thus elevating the level of heat shock proteins in and proximal to infected tissue as a means to invoke an immune response by associating the infected tissue with the elevated heat shock proteins. This localized thermal increase can be achieved using a precise deposition of energy at the location of lesions which is readily achievable using microwave energy. As in the case of HPV this is applicable to any strain of the virus, which overcomes the limitation of a vaccine.

Localised microwave hyperthermia can be used to raise the temperature of the tissue containing the HPV virus thus denaturing the viral particles promoting antibody production to eliminate the virus.

In tissue infected with HPV a network of supply capillaries is generated by the virus to sustain the growth of papillomas such as warts or verrucae. These can be seen as small dark dots close to the surface of the lesion. A number of existing treatments (e.g. cryotherapy, salicylic acid) try to disrupt or damage this blood supply to the lesion in an attempt to alert the immune system to the presence of the virus.

Microwave ablation can be used to coagulate or compromise the function of the blood supply to HPV lesions. The thermal insult and resultant disruption of blood supply to the HPV infected tissue can be used to destroy tissue supported by the capillary feed network resulting in necrosis of the remaining tissue. This technique can also apply to other tissue lesions or growths which have a sustaining blood supply, (e.g. benign growths, skin cancers, neoplasms, moles etc.).

Microwave energy is also suspected of having immunostimulatory properties and as such may also be used as a means to stimulate or enhance an immune response in a subject or host. That immune response may be local to the area targeted by or exposed to the microwave energy. This phenomenon is discussed in more detail below but the stimulated immune response may be sufficient to facilitate the clearance and/or resolution of any of the diseases and/or conditions described herein—including for example, those diseases and/or conditions associated with HPV.

Typically the dielectric properties of materials are measured relative to those of air and referred to as epsilon relative to air (Er) where air is Er=1. The high frequency dielectric properties of tissue infected by HPV have not currently been reported in the literature. The dielectric properties have been measured here and it was found that the dielectric properties of diseased (for example, HPV infected) tissue differed considerably from normal tissue. Thus, applicators that electrically match with the range of epsilon relative values may be used to ensure energy is efficiently delivered into, for example, tissue infected by HPV and/or a papilloma.

For example in the case of Verruca plantaris, excess keratin changes the dielectric constant of the tissue. The dielectric constant of the measured tissue (sample range 7.5-8.5 GHz) was found to lie between Er 2 to Er 10 for dry tissue. The median Er value was measured at 4.93. The 95% confidence interval for the median was found to lie between Er 4 and Er 6.7.

This is in contrast to normal plantar tissue which was found to range between Er 6 to Er 16 for dry skin, with the median Er value measured at 10.6. The 95% confidence interval for this median lies between Er 8.75 and Er 12.3. The measured values of epsilon relative were for dry tissue and will differ in value from other HPV lesions elsewhere on the body, e.g. in mucosal tissues which generally have higher values of epsilon relative due to the presence of water which has an Er of 80-34.5 (depending upon temperature). In these instances the Er may be in the range Er 20-40.

The demarcation between the measured values of epsilon relative for various plantar tissue types was found to decrease with increasing measurement frequency which suggests that at higher frequencies the stratum corneum layer dominates the measurements.

In view of the above, the dielectric properties/constant of diseased or infected tissue (for example tissue infected with or containing HPV) may be lower than that of normal (not diseased or infected) tissue. As such, a tissue dielectric property/constant may form the basis of a procedure or method for the diagnosis or detection of a disease or condition, in particular a disease or condition which alters the dielectric properties of a tissue. For example, tissue dielectric properties may be exploited in methods of diagnosing or detecting diseases and/or conditions characterised by or causing, changes in levels of keratin in tissue(s). As stated, a change in tissue keratin levels (for example the development or production of excess keratin) may occur as a consequence of an HPV infection and may be a feature or characteristic of an HPV papilloma. Thus, a dielectric property or constant may be exploited in a method of diagnosing or detecting an HPV infection or HPV associated disease or condition.

For example, the dielectric constant of test tissue may be compared to a control dielectric constant, wherein if the dielectric constant of test tissue is lower than that of the control dielectric constant, the test tissue may harbour a disease and/or condition characterised by or causing, changes in levels of keratin and/or may contain or be infected with, HPV.

The test tissue may be any tissue (for example a skin or mucosal tissue) vulnerable to HPV infection and/or suspected of containing HPV. The test tissue may comprise tissue from a wart or other lesion suspected of having an HPV aetiology.

A control dielectric constant may be that associated with a tissue which has a normal level of keratin and/or is not diseased or infected (by HPV). For example, where the tissue is plantar tissue, in accordance with the information presented above, a control dielectric constant may range between Er 6 to Er 16 for dry skin, with the median Er value measured at 10.6.

A method of detection or diagnosis as described herein may be performed in vitro or in vivo. An in vitro method may be performed on a sample, for example a tissue biopsy or scraping.

In one application, a procedure or method for the diagnosis or detection of a disease or condition which alters the dielectric properties of a tissue (for example a conditions associated with HPV or a HPV infection) may be conducted on a test tissue of a wart (for example a cutaneous wart or plantar wart) or other lesion suspected of having an HPV aetiology or a biopsy therefrom. Specifically, the dielectric properties of the tissue or sample may be compared to the corresponding control dielectric property from the same or a similar tissue, wherein if the dielectric property (constant) of the test tissue is lower than the corresponding control value, the test tissue may be diagnosed or identified as potentially comprising or being infected with HPV.

A positive "HPV" diagnosis may then lead to the use of any one of the microwave energy techniques described herein to resolve the relevant disease or condition.

As a penetration depth of a few mm may be required a frequency in the range 5.8 GHz to 15 GHz is may be desirable as higher frequencies may not penetrate sufficiently. The power level and energy density of application will also affect the depth of penetration therefore lower frequencies may be used with appropriately designed applicators and treatment profiles.

The present invention is based on the finding that microwave energy may be used to treat diseases and/or conditions having a microbial (particularly HPV), genetic, allergic, autoimmune and/or malignant (cancerous) aetiology.

Thus disclosed herein is a method of treating or preventing a disease and/or condition caused or contributed to by human papilloma virus (HPV), a malignant condition (including any with a HPV aetiology) and/or a dermatological condition including those in which tissue (for example skin) is infected with one or more microbial (for example viral) pathogen(s) said method comprising administering to a subject, a therapeutically effective amount or dose of microwave energy.

The method may be applied or administered to a human or animal subject and to any tissue or region thereof. The subject may be any subject having or suffering from any disease and/or condition caused or contributed to by a human papilloma virus (HPV), a malignant condition (including any with an HPV aetiology) and/or a dermatological condition including those in which tissue (for example skin) is infected with one or more microbial (for example viral) pathogen(s) or a subject predisposed or susceptible thereto.

The method may be applied or administered to the skin and/or mucosal tissues and/or to any cervical, respiratory, head, neck, genital, anal, plantar and/or oral locations.

Also disclosed herein is microwave energy for use in treating or preventing any disease and/or condition caused or contributed to by a human papilloma virus (HPV), a malignant condition (including any with an HPV aetiology) and/or a dermatological condition including those in which tissue (for example skin) is infected with one or more microbial (for example viral) pathogen(s).

One of skill will appreciate that in order to resolve any of the diseases and/or conditions described herein and/or reduce the symptoms thereof, one or more treatments with microwave energy may be required.

Without wishing to be bound by theory, the inventors hypothesise that the induction of hyperthermia by targeted application of microwave energy, induces the production of heat shock proteins in diseased or damaged tissue. This may lead to the activation of antigen presenting cells (such as dendritic/langerhans cells) which process antigen (including host, microbial or other foreign antigen) for presentation to T cells. Furthermore, the induction of hyperthermia may inhibit phosphoinositide 3-Kinase (PI3-K) in Langerhans cells facilitating the induction of a potent host immune response. Localized thermal increase can be achieved using a precise deposition of energy to a diseased tissue (for example a lesion), readily achievable using microwave energy.

Further, it has been noted that when used at energy levels which do not result in any substantial tissue/cell damage and/or ablation, subjects still exhibit good clinical responses. Again, without wishing to be bound by theory, the microwave energy based treatments described herein have been shown to induce an immune response which facilitates the (at least partial) clearance and/or resolution of a dermatological disease and/or condition. The immune response may be a partially or fully protective immune response. The immune response may be a local response—that is a response which "local" to the site of microwave energy treatment or the disease and/or condition to be treated. The immune response may be a cell-based immune response involving the induction, proliferation and/or activation of one or more innate immune system mechanisms/pathways, immune system cells (T cells and the like) and/or cytokines. Thus, there is provided a method of stimulating an immune response in a subject, said method comprising administering a subject an amount or dose of microwave energy. Further, there is provided, microwave energy for use in a method of stimulating an immune response in a subject. As stated, the immune response may be a local response and/or a cell/cytokine based response.

The subject may be any subject diagnosed as suffering from any of the diseases and/or conditions described herein. Additionally, or alternatively, the subject may be susceptible or predisposed to any of the diseases and/or conditions described herein.

Thus, in one application, a method of raising an immune response via the use of microwave energy may be applied to a subject suspected of suffering from one or more HPV associated warts or lesions. In such circumstances, the method may involve applying microwave energy to a wart or lesion so as to induce a local immune response. As stated, the raised immune response may then be sufficient to resolve the one or more wart(s) or lesion(s).

The method of stimulating an immune response in a subject may exploit microwave energy applied at a level which does not result in any substantial macroscopic and/or histological changes in the tissue subjected to the microwave treatment. The microwave energy may be used at a level which is sub-apoptotic and/or which induces in human skin, mild macroscopic epidermal changes, microscopically minor architectural changes and slight elongation of keratinocytes without evidence of dermal collagen sclerosis. Higher levels of microwave energy may be used (for example 100J or >100 J) and this may result in more significant dermal and/or epidermal changes, including gross tissue contraction, spindled keratinocytes with linear nuclear architectural changes and subepidermal clefting. The microwave energy may be applied at a sub-clinical level, that is an energy level which might not in itself result in resolution or clearance of the disease or condition (for example wart) affecting the targeted tissue.

The microwave energy may be applied at an energy of anywhere between about 1 J and about 500 J, for example, about 5 J to about 200 J. The microwave energy for use in a method of stimulating an immune response in a subject may be used at about 5 J, about 10 J, about 50 J, about 100 J or about 200 J.

The microwave energy for raising or stimulating an immune response may be applied for any suitable duration of time. The microwave energy may be applied for anywhere between about 0.1 s and about 1 minute. The microwave energy may be applied for about 1 s, about 5 s about 10 s, about 20 s or about 30 s. The microwave energy may be applied as multiple bursts or pulses of the same or different duration and/or of (or at) the same or different energy level. Each applied microwave energy burst/pulse may last for the same or a different duration. An applied amount of microwave energy may be described as a "microwave energy dose"

A subjected may be delivered one or more microwave energy doses over a predetermined period of time. For example, a subject may be administered a single dose on 1 day or multiple doses over the same day, each dose being separated by a non-dosing period. Additionally or alternatively, a subject may be administered other doses on subsequent days. A treatment (comprising one or more microwave energy doses) may last a day, multiple days or one or more weeks months or years.

Where the lesion (wart or the like) to be treated is small, for example less than about 7 mm in diameter, a single dose may be applied to a single site within, on or to the lesion. Where the lesion is larger, for example larger than about 7 mm, the lesion may be applied multiple doses in a manner that ensures that the entire surface or area of the lesion has been exposed to microwave energy.

The immune response stimulated or induced by the methods described herein may comprise the activation of certain cell types, increased antigen presentation and/or modulated cytokine production. More specifically, an immune response stimulated or induced by a microwave energy based method of this invention may comprise keratinocyte activation, enhanced signalling between keratinocytes and dendritic cells which in turn enhances the level of HPV antigen cross-presentation to CD8+ T lymphocytes and enhanced IL-6 synthesis from keratinocytes.

One of skill will note that IL-6 is a pro-inflammatory cytokine which an important role in anti-viral immunity and which has been shown to induce rapid effector function in CD8+ cells. As such (and without wishing to be bound by theory), the microwave energy based methods described herein, which methods induce IL-6 synthesis, may facilitate the induction of a cytokine based anti-viral immunity.

Additionally, it has been shown that the microwave energy based methods of this invention might modulate certain other aspects of the host immune response. For example, the microwave energy may modulate interferon regulatory factor (IRF) expression. IRFs have been shown to be central to the regulation of an immune response. For example, IRF4 is essential for cytotoxic CD8+ T cell differentiation and its up-regulation in dendritic cells has been shown to enhance CD4+ differentiation, thereby potentially enhancing both CD8+ immunity and T cell help following microwave treatment. IRF1 expression has also been implicated in the modulation of HPV infection. It has been found that IRF1 expression is down-regulated in response to the application of microwave energy and thus IRF1 may represent another therapeutic target for the treatment and/or prevention of an HPV infection.

Thus the microwave energy based immunostimmulatory methods of this invention might be used to achieve any one or more of the following:
  (i) modulation of immune cell activation;
  (ii) modulation of antigen presentation;
  (iii) modulation of cytokine expression; and/or
  (iv) modulation of IFR.

As stated, the stimulated immune response may be effective to facilitate the resolution and/or clearance of one or more dermatological diseases and/or conditions including, for example, HPV based infections, HPV based cancers and/or lesions. A detailed discussion of these terms is provided in the paragraphs that follow.

The term "dermatological diseases and/or conditions" as used herein, relates to pathological diseases and/or conditions affecting the skin and/or associated tissues. However, the present invention may extend to the treatment of diseases and/or conditions of the integumentary system, including, for example, the mucosal membranes of the respiratory, gastrointestinal and genitourinary systems. One of skill will appreciate that dermatological tissues may comprise epidermal, dermal and/or sub-dermal tissues of the skin as well as other layers, such as the stratum corneum, stratum lucidum, stratum granulosum, stratum spinosum and stratum basale which lie within. Additionally, the term dermatological condition relates to conditions which affect the cosmetic appearance of the skin. Such cosmetic conditions may include the presence of papillomas (warts), marks, scars or calluses.

In one embodiment, the dermatological disease and/or condition is caused or contributed to by a cell/tissue proliferation and/or differentiation disorder such as, for example, cancer. As such, the disease and/or condition to be treated may include skin or cervical cancer. The cancer may be an HPV-positive cancer; that is a cancer caused or contributed to by HPV. HPV is known to be associated with many different forms of cancer and therefore, the dermatological disease and/or condition may be HPV associated (or positive) oropharyngeal cancer (particularly cancer occurring on the tonsil(s) and/or at the base of the tongue), oesophagus cancer (including, for example, some stomach cancers), oral cancer, anal cancer, lung cancer, cervical cancer and anogenital tract cancer. For convenience all of these (and any other) HPV-positive cancers shall be collected together under the general terms "malignancy" or "cancer".

In some cases, the disease and/or condition results in the appearance of benign or malignant lesions. In other embodiments, the dermatological disease and/or condition may result from some uncontrolled accumulation or proliferation of connective tissue or extracellular substance, leading to, for example, keloid lesions and the like.

Dermatological diseases and/or conditions may also include autoimmune, allergic and/or hypersensitivity related pathologies such as, for example, psoriasis, eczema, icthyosis vulgaris, sclerodema and/or lupus.

In other cases, the dermatological disease and/or condition may, for example, take the form of a lesion and may be caused or contributed to by one or more microbial infections including, for example, fungal, bacterial and/or viral infections. In particular, the invention relates to the treatment of viral skin infections such as those related to or associated with human papillomavirus (HPV). In particular, the present invention finds application in the treatment of papillomas and warts (for example cutaneous warts) as well as other lesions caused or contributed by a microbial organism such as a virus. The methods presented in this application may find application in the treatment and/or prevention of plantar warts otherwise known as verruca plantaris caused by HPV.

One of skill will appreciate that unlike with vaccines which are specific to a particular species of organism and, in some cases, one or a very limited number of specific species strains, microwave energy may be used to treat dermatological diseases and/or conditions irrespective of the species/strain type. This is particularly important for HPV infections where a large number of different strains are known to be responsible for disease.

One of skill will appreciate that any method in which an immune response can be stimulated, enhanced or induced at the site of a disease and/or condition (for example a HPV lesion), may represent an improvement over prior art methods which focus of the direct and individual treatment of each lesion. A method which stimulates, enhances or induces some form of local (cell and cytokine) based immune response at a single site of infection may facilitate the clearance of a number of similar lesions in the same area. Were the lesion to be treated has a microbial (for example HPV) aetiology, a treatment method which stimulates a local cell based or innate immune response, might addresses some of the issues associated with vaccines which tend to induce immune responses which are specific to certain microbe strains.

As such, one embodiment, of this invention provides a method of treating or preventing HPV infections, said method comprising administering a therapeutically effective amount or dose of microwave energy to a subject having or suffering from an HPV infection or a subject susceptible or predisposed to an HPV infection. In one embodiment, the microwave energy may be directed to a lesion or wart, for example a plantar or cutaneous wart (or verruca), associated with an HPV infection.

The invention also provides microwaves or microwave energy for use in treating or preventing HPV infections and/or HPV associated cancers (as described above) as well as microwaves for use in treating, resolving, removing or reducing warts, for example plantar warts (or verrucas) associated with an HPV infection.

Again, without wishing to be bound by any particular theory, the inventors suggest that the application of mild localized hyperthermia of a pulsed nature may inhibit PI3-K helping the immune system in identifying the underlying HPV infection promoting Langerhans cells and heat shock proteins to identify and present the HPV virus to the immune system causing a localized inflammatory response. Further, the immunostimulatory effect of microwave energy may further facilitate resolution and/or clearance of a disease or condition caused or contributed to by an HPV infection.

In a further aspect, the invention provides a method of cosmetically improving the appearance of a part of the body, comprising administering to a subject an amount or dose of microwave energy effective to cosmetically improve the appearance of a part of the body and optionally repeating said treatment until a cosmetically beneficial improvement in appearance has occurred. The method of improving bodily appearance may be used to improve the appearance of a subject's skin and may be used to remove defects of the skin including marks, scars, papillomas (including warts), calluses and the like.

Microwave energy according to this invention may have a frequency of between about 500 MHz and about 200 GHz. In other embodiments, the frequency of the microwave energy may range from between about 900 MHz and about 100 GHz. In particular, the frequency of the microwave energy may range from about 5 GHz to about 15 GHz and in a specific embodiment has a frequency of 8 GHz.

It should be understood that the methods of treatment described herein may require the use of a microwave energy having a single frequency or microwave energy across a range of frequencies.

The invention further provides an apparatus for use in treating any of the dermatological conditions and/or diseases described herein, said apparatus comprising a microwave source for providing microwave energy and means for administering or delivering the microwave energy to a subject to be treated. The apparatus provided by this aspect of the invention may be used in any of the therapeutic methods described herein.

Advantageously, the microwave energy emitted or produced by the apparatus elevates or raises the temperature of the subject to be treated and/or stimulates a local immune response as described herein. In one embodiment, the microwave energy may cause targeted or localised hyperthermia in a tissue of the subject, including, for example the skin and/or mucosal membrane. The temperature elevation may be localised to the surface of the skin and/or to the epidermal, dermal and/or sub-dermal layers thereof (including all minor layers that lie within).

The apparatus may further comprise means for controlling at least one property of the microwave energy produced by the microwave source. For example the means may control or modulate the power, frequency, wavelength and/or amplitude of the microwave energy. The means for controlling the microwave energy may be integral with the apparatus or separately formed and connectable thereto.

In one embodiment, the microwave energy source may produce microwave energy at a single frequency and/or microwave energy across a range of frequencies. The means for controlling at least one property of the microwave energy may permit the user to select or set a particular microwave or microwaves to be produced by the apparatus and/or the properties of the microwave(s) produced.

The apparatus may further comprise means for monitoring the microwave energy produced or generated by the microwave source. For example, the apparatus may include a display indicating one or more properties of the microwave energy.

In one embodiment, the means for administering or delivering the microwave energy to a subject to be treated comprises an applicator formed, adapted and/or configured to deliver or administer microwave energy to the subject. The inventor has discovered that the dielectric properties of tissue affected by a dermatological disease and/or condition vary with respect to normal, healthy, tissue (i.e. tissue not affected by a dermatological disease and/or condition). As such, the means for delivering microwave energy may electrically match the range of epsilon relative values of the tissue affected by a dermatological disease and/or condition. In this way, it is possible to ensure efficient delivery of the microwave energy to the tissue.

Advantageously, the means for delivering the microwave energy to a subject may comprise a component or part for contact with a subject to be treated. The part or component for contact with the subjected to be treated may be removable such that it can be discarded or sterilised after use. In one embodiment, the means for delivering the microwave energy may comprise a single application element or a hand piece which accepts a removable tip which can either be a single use, disposable component or a reusable component intended to be sterilized between uses. Advantageously, the part or component for contact with the subject to be treated may comprise a reuse mitigation function to prevent accidental or attempted reuse.

In one embodiment, the part or component for contact with the subjected to be treated may be shaped, formed or adapted so as to be compatible with a particular internal or external body part, surface or lesion thereof. For example, the part or component may comprise a domed, curved or enclosing surface, compatible with the physical properties or profile of an internal or external body part, a surface or a lesion thereof, including, for example a papilloma such as a wart or verucca.

The means for delivering the microwave energy to a subject may be connected to the microwave source via a flexible cable. In one embodiment the means for delivering the microwave energy to a subject (i.e. the applicator) may be connected to the microwave source via a flexible cable with locking connections having both microwave and signal data cables and may be reversible to enable connection to either port.

In one embodiment the invention provides an apparatus for delivering microwave energy to infected tissue the apparatus comprising:—a microwave source for providing microwave energy, connectable to a system controller for controlling at least one property of the microwave radiation provided by the microwave source; and a monitoring system for monitoring the delivery of energy and an applicator means, for example an applicator device, for delivering microwave energy, wherein:—the applicator is configured to deliver precise amounts of microwave energy provided by the source at a single frequency or across a range of frequencies.

A further embodiment of this invention provides a method for treating or preventing any of the dermatological diseases and/or conditions described herein and/or an (HPV) infected tissue, said method comprising the administration or delivery of a therapeutically effective and/or immunostimulatory dose or amount of microwave energy to infected or diseased tissue to produce, induce or elevate and immune response and/or levels of heat shock factor HSF to stimulate production of heat shock proteins in or near the tissue. In particular, the method for treatment may produce, induce or elevate levels of one or more heat shock proteins selected from the group consisting of HSP90, HSP72, HSP70, HSP65. HSP60, HSP27, HSP16 and any another heat shock protein(s) wherein:—the microwave energy promotes an association between the elevated heat shock proteins and the infected tissue so as to elicit an immune response against the infection. Additionally or alternatively, the microwave energy may be sufficient to induce a local immune response which comprises modulated cell and cytokine induction/expression/activation and enhanced antigen presentation.

In a further embodiment of the invention there is provided a method for the treatment of a lesion, in particular a lesion associated with an HPV infection, said method comprising administering or delivering a therapeutically effective and/or immunostimulatory amount or dose of microwave energy to a lesion, wherein the microwave energy induces a local immune response effective to facilitate resolution or clearance of the lesion and/or cauterises, coagulates, shrinks, blocks, ablates, damages, irritates, inflames or otherwise interferes with the normal operation of the capillaries supplying blood to the lesion. In one embodiment the lesion is a skin lesion including, for example, warts, verrucae, benign growths, skin cancers, moles and the like.

In a further embodiment, the present invention provides a method for the treatment of a viral lesion, said method comprising the step of delivering or administering a therapeutically effective or immunostimulatory amount or dose of microwave energy to the lesion, wherein the microwave energy stimulates an anti-viral immune response and/or causes the denaturing of viral particles within the lesion thus exposing antigenic sites stimulating to further enhance an immune response. In one embodiment the viral lesion is a viral skin lesion such as, for example a warts, verruca, benign growth, cancer and the like.

In another embodiment, the present invention provides a medical treatment regime comprising:—the application of microwave energy to infected skin tissue to purposefully elevate levels of heat shock factor HSF to stimulate production of heat shock proteins in or near the tissue in particular HSP90, HSP72, HSP70, HSP65. HSP60, HSP27, HSP16 and any another heat shock protein(s) wherein the microwave energy promotes an association between the elevated heat shock proteins and the infected tissue with the intention to provoke an immune response against the infection In a further embodiment, the present invention provides a medical treatment regime comprising:—the application of microwave energy into infected skin tissue to purposefully cauterise, coagulate, shrink, block, ablate, damages, irritate, inflame or otherwise interferes with the normal operation of the capillaries supplying blood thus causing necrosis of the lesion.

In another embodiment, the present invention provides a medical treatment regime comprising:—the application of microwave energy into tissue infected with a virus such as human papillomavirus to purposefully denature the viral particles with the intention of exposing antigenic sites thus stimulating an immune response to the virus.

There is also provided a medical treatment regime comprising the application of microwave energy into tissue infected with a virus such as human papillomavirus to stimulate an immune response, which immune response comprises modulated cell and/or cytokine induction/expression/activation and/or enhanced antigen presentation.

Any feature in one aspect of the invention may be applied to any other aspect of the invention, in any appropriate combination. For example, apparatus features may be applied to method features and vice versa.

BRIEF DESCRIPTION OF THE DRAWINGS

Embodiments of the invention are now described, by way of non-limiting example, and are illustrated in the following figures, in which:—

FIG. 10A: Clinical image of plantar wart pre-microwave treatment (left), after one treatment (middle) and after two treatments (right). FIG. 10B: Clinical image of plantar wart pre-microwave treatment (left), after one treatment (right).

FIG. 13C: Flow cytometric analysis of intracellular HSP-70 expression on viable keratinocytes after microwave therapy or control depicted as a histogram. Primary human keratinocytes were treated with microwave therapy (150 J), or nil (untreated), rested in culture for 24 hours, before analysis. X-axis: MFI anti-HSP-70; y-axis: cell count

DETAILED DESCRIPTION OF EMBODIMENTS

Figure 1:
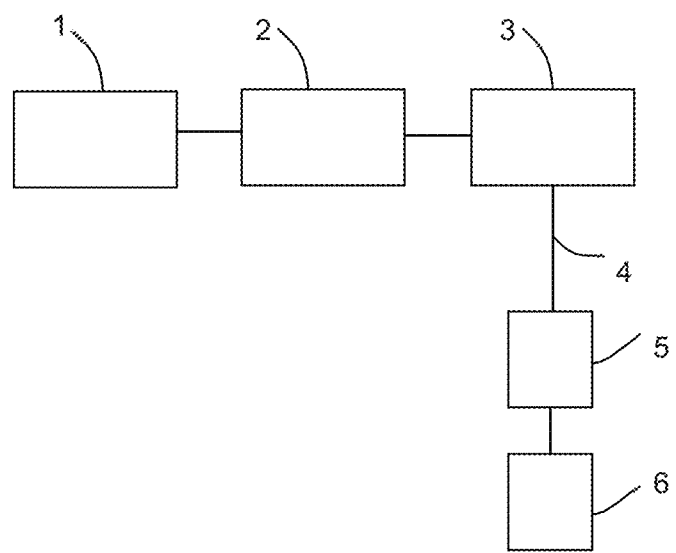
FIG. 1 is a schematic illustration of an embodiment of a microwave treatment system.

An embodiment of a microwave power generator system for medical applications is illustrated in FIG. 1 The apparatus comprising:—a microwave source for providing microwave energy 1, connectable to a system controller 2 for controlling at least one property of the microwave radiation provided by the microwave source; and a monitoring system 3 for monitoring the delivery of energy and an interconnecting cable 4 and an applicator hand piece 5 and a removable applicator means 6, for example an applicator device, for delivering microwave energy, wherein:—the applicator is configured to deliver precise amounts of microwave energy provided by the source at a single frequency or across a range of frequencies.

Figures 2A, 2B:
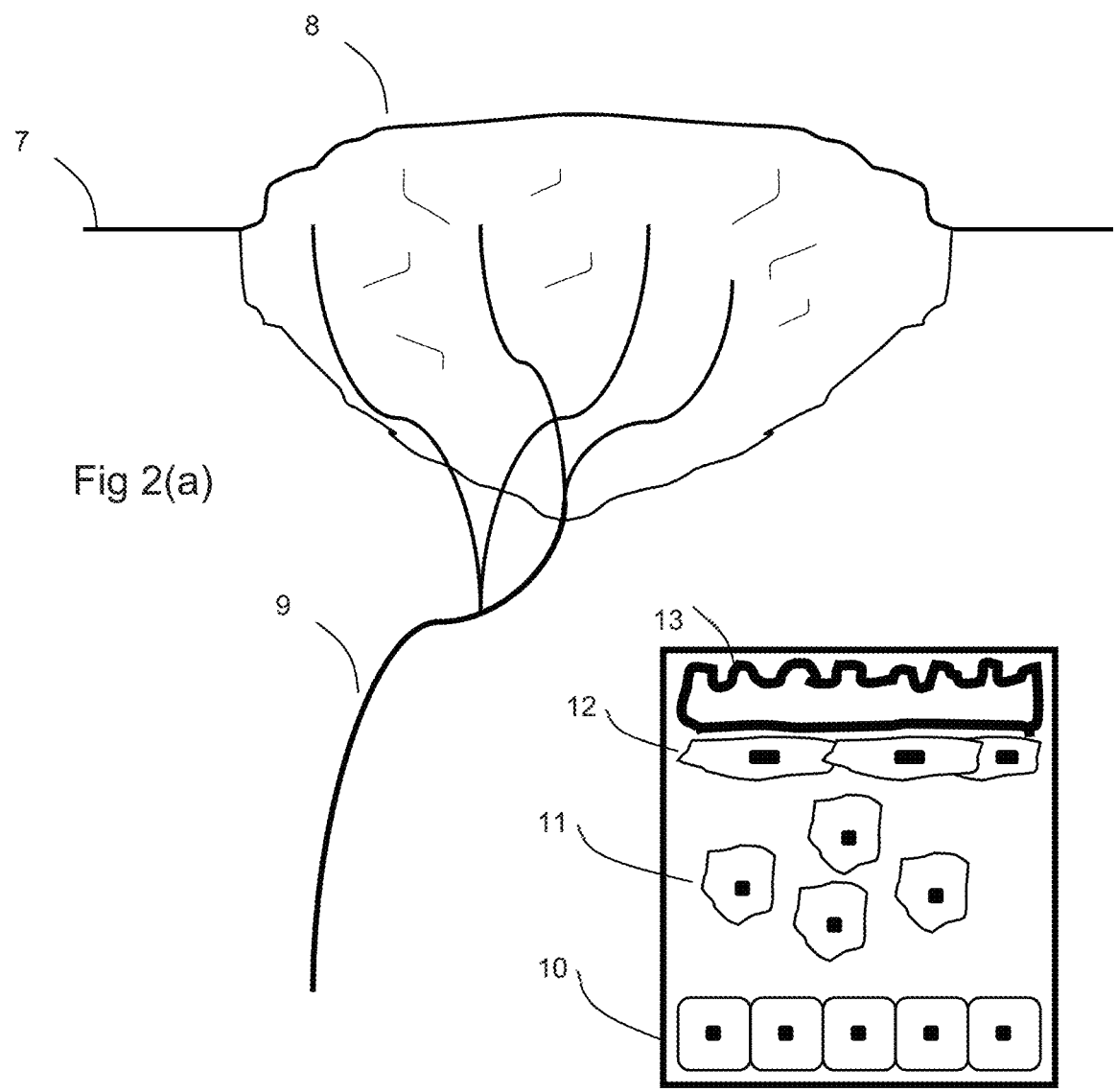
FIG. 2(a) is a schematic illustration of a Papilloma caused by HPV infection.
FIG. 2(b) is a schematic illustration of the terminal differentiation pathway of epidermal cells infected by the HPV virus.

A typical HPV infection is illustrated in FIG. 2(a), this comprises the normal tissue 7, the papilloma surface 8, the capillary feed network 9. The terminal differentiation pathway of epidermal cells infected by the HPV virus is illustrated in FIG. 2(b) basal cells 10 become infected with the HPV virus leading to viral replication in the stratum spinosum 11 followed by assembly of virus particles in the stratum granulosum and release of virus particles in the in the stratum corneum (papilloma surface).

Figure 3:
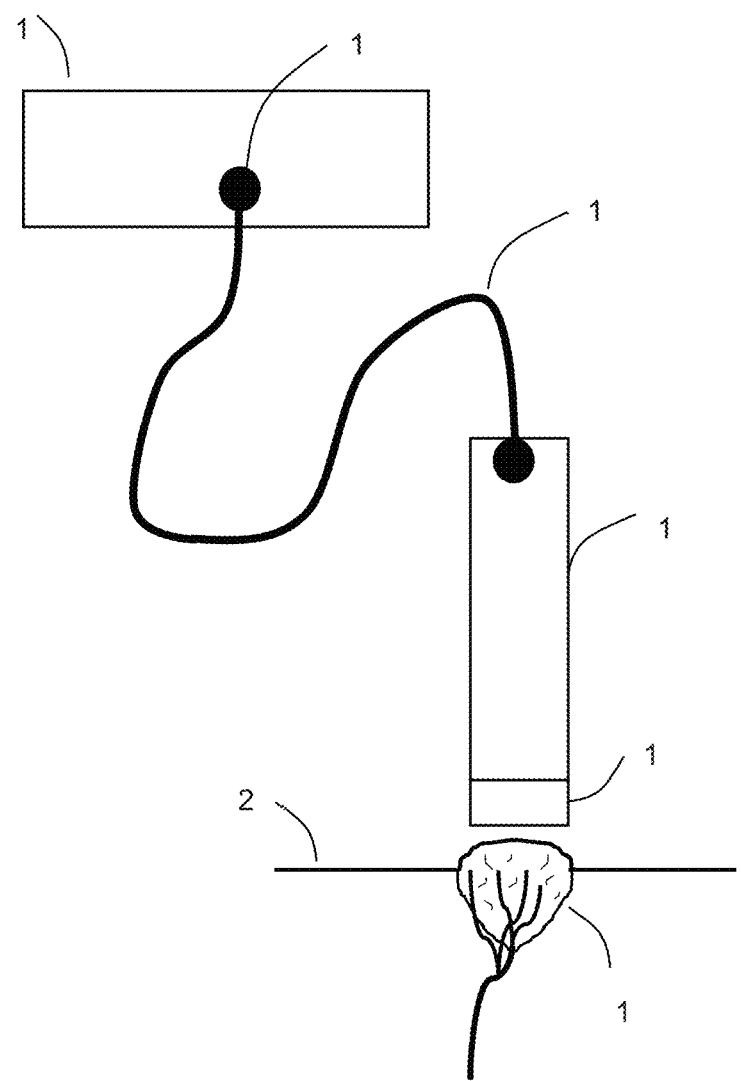
FIG. 3 is a schematic illustration of functional representation of a microwave treatment system for application to treat Papilloma or other dermatological lesions.

FIG. 3 shows the components of an apparatus according to an embodiment of the present invention, the components shown separately for ease of reference. The apparatus comprises a generator system 14 with a locking microwave connection 15 to a flexible microwave cable 16 connected to a hand piece 17 (which may have the same type of locking connection) which accepts an applicator component 19. The applicator component is designed to match to the tissue properties of the papilloma 20 and not match to the normal tissue 18. The cable 16 may include both microwave and signal data cables and may be reversible to enable connection to either port.

Figure 4:
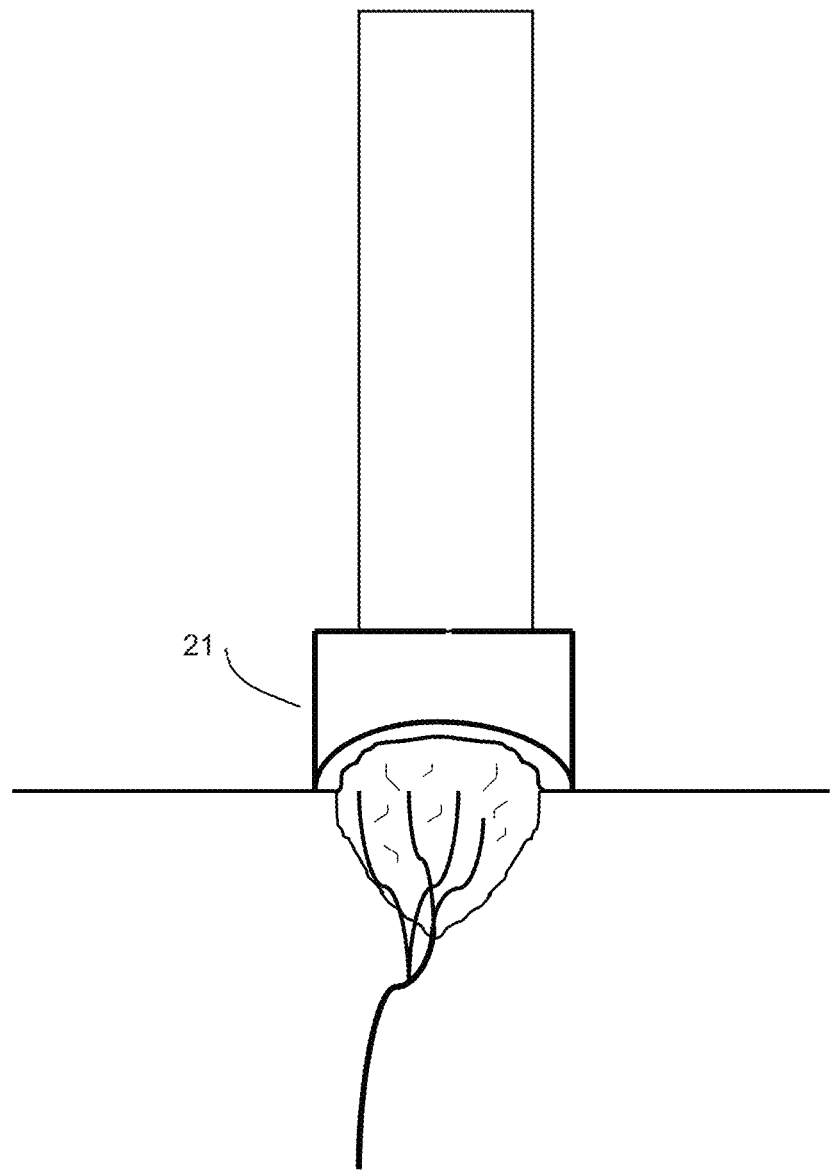
FIG. 4 is a schematic illustration of a microwave treatment system applicator according to an alternative embodiment.

An alternative embodiment of an applicator 21 is illustrated in FIG. 4 with the component having a domed or enclosing surface compatible with raised or curved lesions.

Figure 5:
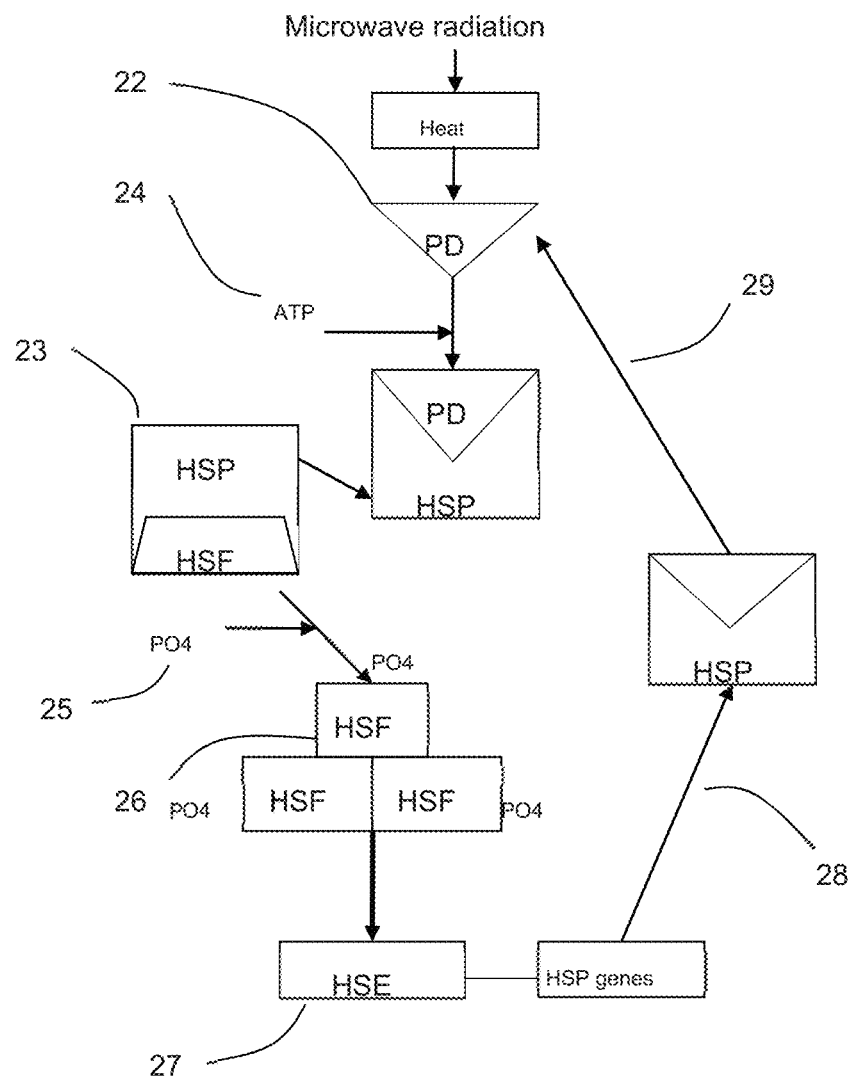
FIG. 5 is a schematic illustration of the microwave activation of the heat shock response.

The method of inducing a microwave heat shock responses is illustrated in FIG. 5. In this illustration microwave radiation creates a thermal stress which results in protein denaturation 22. Heat shock proteins (HSP) are normally bound to heat shock factors (HSF) (23), but dissociate in the presence of denatured proteins (PD). Once dissociated, HSPs bind to the denatured proteins by rapid release. This requires Adenosine Triphosphate (ATP) 24. Further HSPs are generated when HSFs phosphorylate (PO4) (25) and trimerize (26). These trimers bind to heat shock elements (HSE) 27 that are contained within the promoters of the HSPs and generate more protein 28. Newly generated HSPs can then free to bind more denatured proteins 29.

Figure 6A:
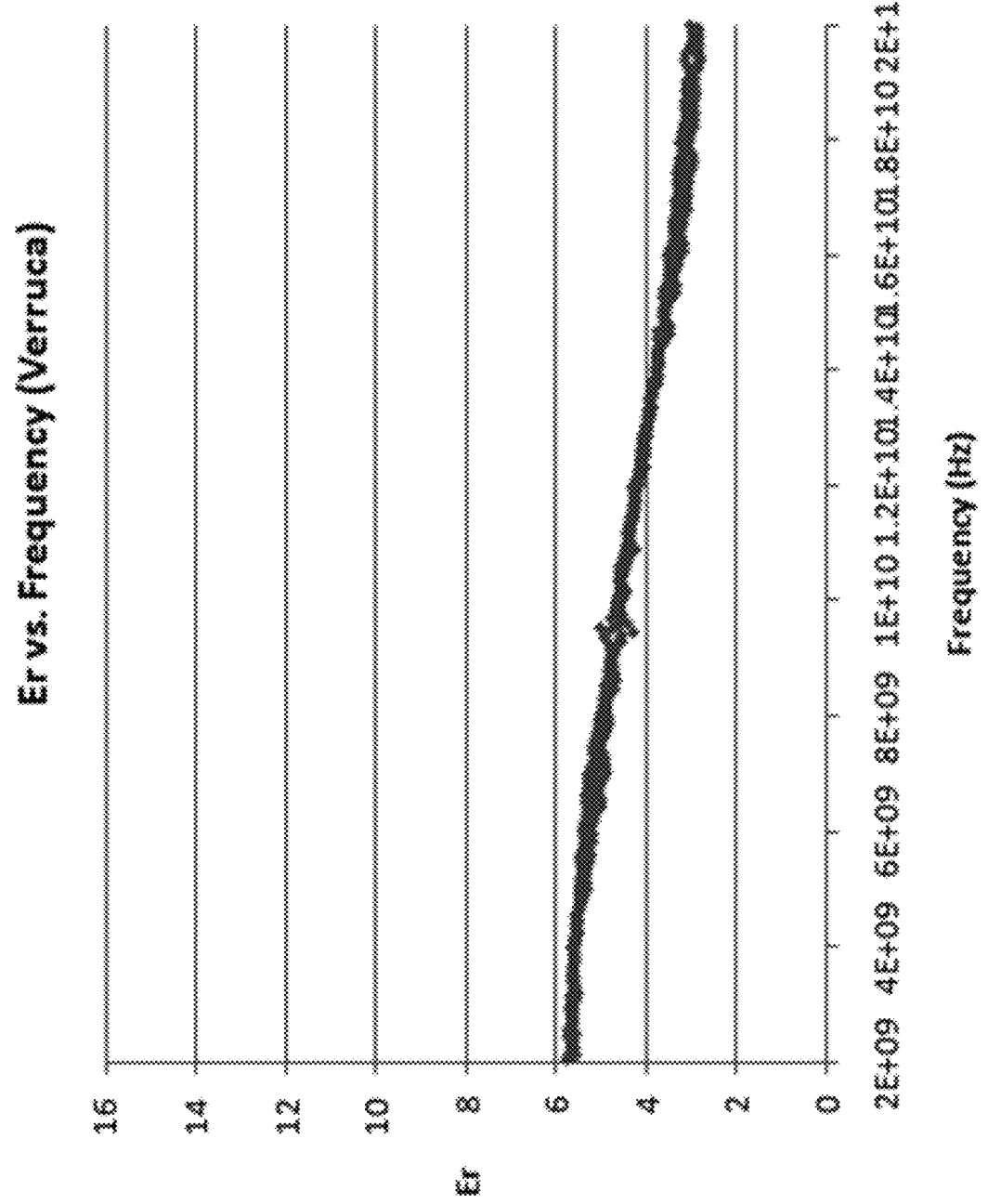
FIG. 6(a) is a schematic illustration of measurement results of Er vs. Frequency for verrucae tissue for a sample population.
Figure 6B:
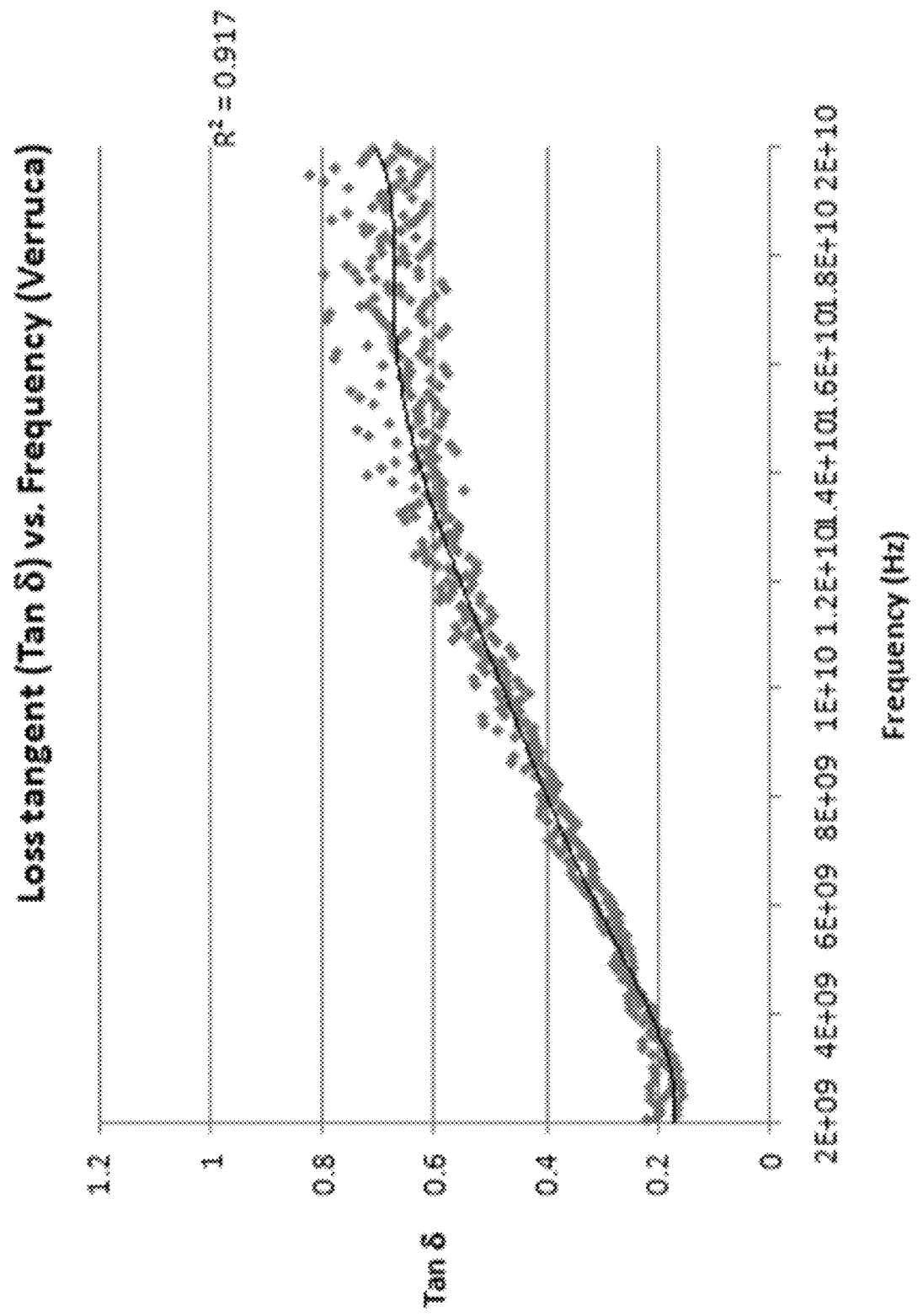
FIG. 6(b) is a schematic illustration of results of Loss tangent vs. Frequency for verrucae tissue for a sample population.

The measured dielectric properties for the sample population median versus frequency of plantar verrucae are reported in FIGS. 6(a) and 6(b). Measured results for ER and loss tangent versus frequency from 2 GHz to 20 GHz are reported. The measurements were made using an Agilent PNA-L Network Analyzer connected to an Agilent 85070E dielectric measurement system with the 85070E Performance Probe Kit (Option 050) measuring from 300 kHz to 20 GHz. Deionised water and air were used as dielectric references for calibration.

Figure 7:
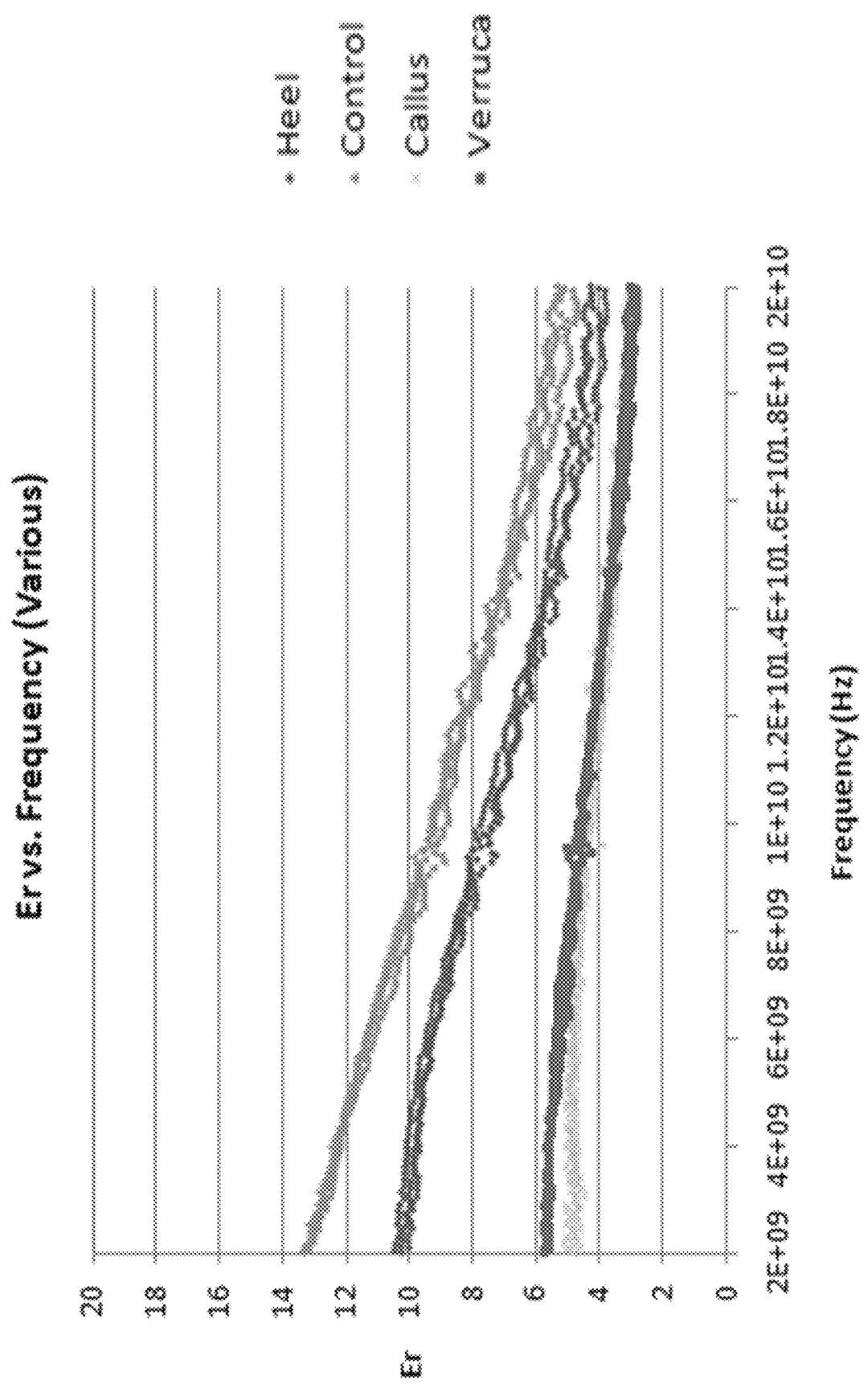
FIG. 7 is a schematic illustration of Er vs. Frequency for various plantar tissues for a sample population.

The measured dielectric properties for the sample population (median taken across the population) versus frequency for various plantar tissues are reported in FIG. 7. Measured results for Er versus frequency from 2 GHz to 20 GHz are reported illustrating demarcation between each tissue type.

Figure 8:
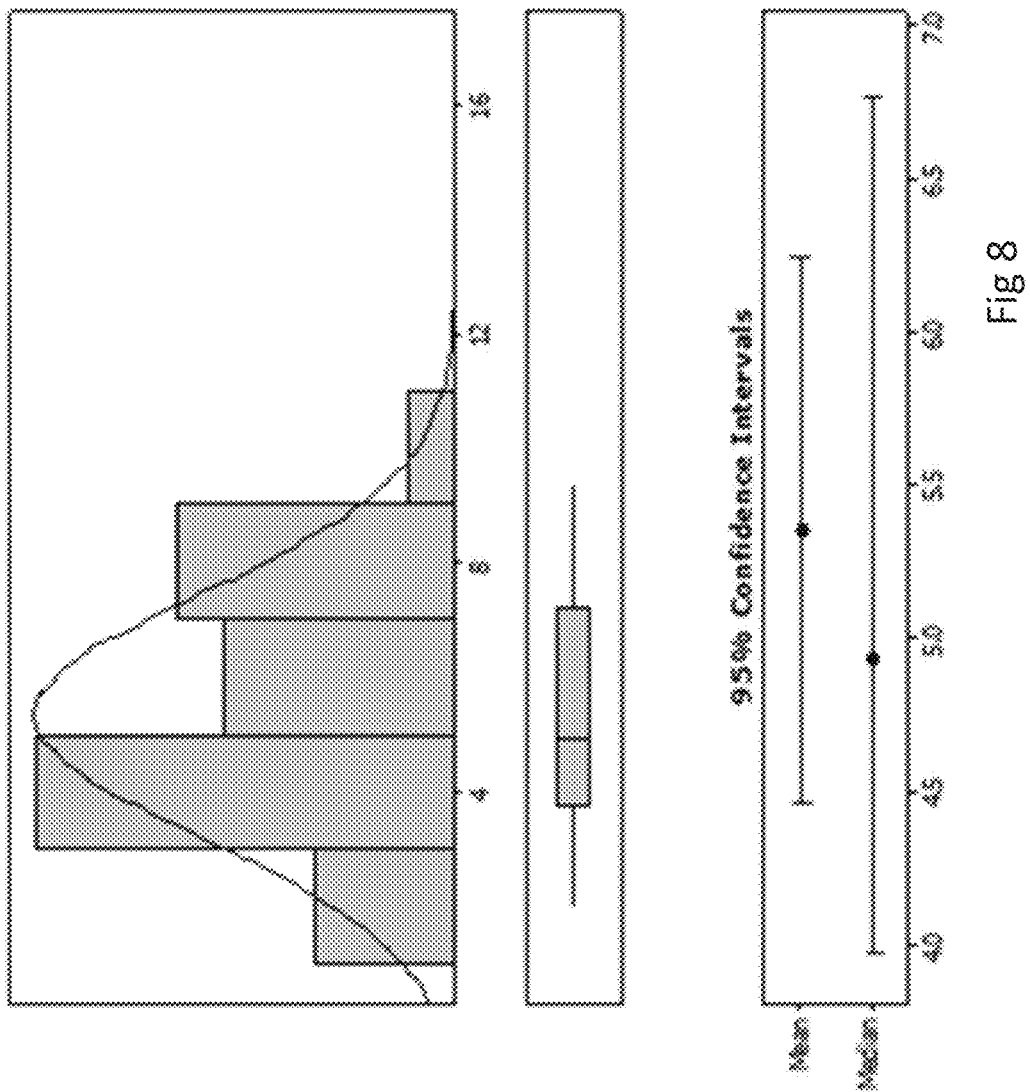
FIG. 8 is a schematic illustration of the statistical analysis of the sample median of verrucae tissue for a sample population.

Statistically analysed dielectric property values taken over a sample population (using the median of the measurement range 7.5-8.5 GHz taken from each sample) for Verrucae tissue is presented in FIG. 8. The median Er value was measured at 4.93 for this dataset.

Figure 9:
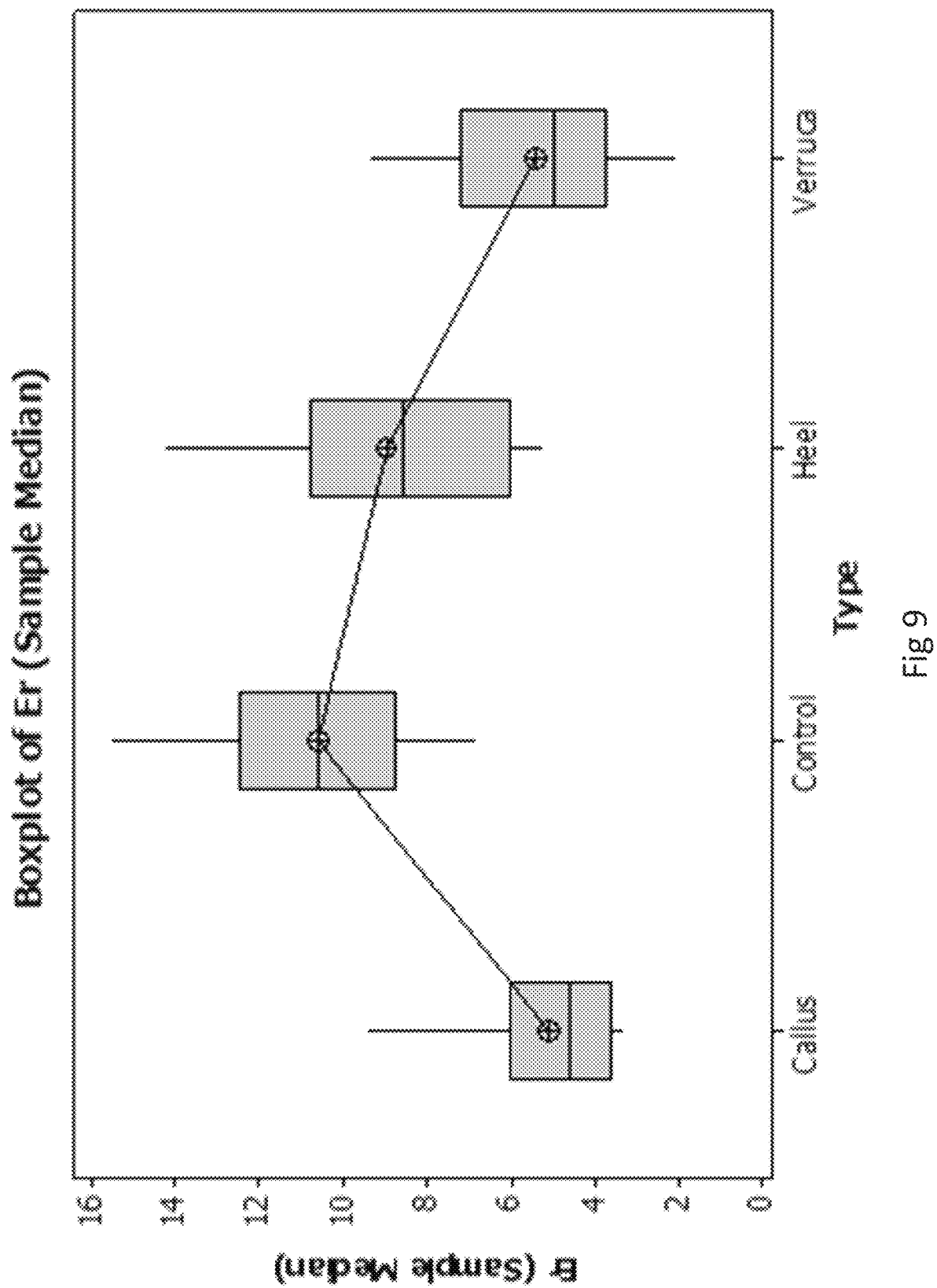
FIG. 9 is a schematic illustration of a comparison of the statistical analysis of sample medians of various plantar tissues for a sample population.

With reference to FIG. 9 a comparison of statistically analysed measurements of the dielectric properties of various plantar tissues over a sample population (using the median of the measurement range 7.5-8.5 GHz taken from each sample) is illustrated.

Microwave Therapy for Cutaneous Human Papilloma Virus Infection
Methods and Materials
Patients and In Vivo Microwave Treatment Patients with treatment-refractory plantar warts were excluded if they had a pacemaker fitted, were pregnant or breast feeding, had any metal implants within the foot or ankle, suffered any known disease or condition affecting their immune function or their capacity to heal. Adverse events were categorized as being specifically associated with the microwave procedure, or unrelated. A complete examination of the affected area was undertaken at each study visit. At the conclusion of the treatment session all patients were given an advice information sheet advised to report any complications. No post-operative dressing was required and patients were advised to subsequently undertake normal everyday activities as usual with no restrictions.

A total of 32 patients with 54 foot warts were enrolled into the study. Of the 32, 17 were males and 15 females. Ages ranged from 22-71 years with a mean age of 44.79 years (sd 13.019]. Of the 54 lesions, 16 were reported as single lesions, and 38 as multiple type lesions (including mosaic verrucae). The average lesion duration was 63 months (5.25 years) with a range of 2-252 months (<1-21 years). The mean lesion diameter was 7.43 mm (sd 6.021), ranging from just 2 mm to 38 mm in diameter.

The procedure was performed in an out-patient setting, with standard podiatric facilities. The Swift device settings were titrated up as tolerated to 50 J over a 7 $mm^2$ application area (7.14 $j/mm^2$). The microwave energy was delivered to the affected area over 5 s duration (50 J delivered as 10 watts for 5 s). Lesions which were <7 mm in diameter were treated with one application of the probe at a single treatment session whilst lesions >7 mm were underwent multiple applications until the entire surface of the wart had been treated.

Clinical assessments were performed at baseline and at 1 week, 1 month, 3 months, and 12 months after treatment by a podiatrist experienced in the management of plantar warts. Response to treatment was assessed by the same investigator as 'completely resolved' or 'unresolved'. Complete resolution was indicated by fulfilling three criteria: i. lesion no longer visible, ii. return of dermatoglyphics to the affected area, iii. no pain on lateral compression. Pain was assessed using a 10 point visual analogue scale.

Human Skin and Ex Vivo Microwave Treatment

Normal skin samples were acquired from healthy individuals after obtaining informed written consent with approval by the Southampton and South West Hampshire Research Ethics Committee in adherence to Helsinki Guidelines. Skin samples were treated immediately ex-vivo with microwave (Swift s800; Emblation Ltd., UK) or liquid nitrogen therapy and treated skin excised. Excised skin was sent for histological analysis or placed in culture media.

Histological analysis with hematoxylin and eosin (H&E) tissue sections were undertaken following fixation and embedded in paraffin wax. DNA damage was assessed by staining for single stranded and double stranded DNA breaks by TUNEL assay using the ApopTag® In Situ Apoptosis Detection Kit (Millipore, UK). Following culture, supernatants were collected and analysed for lactate dehydrogenase release using the Cytotoxicity Detection Kit (Roche applied science) as a measure of apoptosis.

Culture and In Vitro Microwave Treatment.

Human skin and HaCaT keratinocytes were cultured in calcium-free DMEM (ThermoFisher Scientific) with 100 U/mL penicillin, 100 µg/mL streptomycin, 1 mM sodium pyruvate, 10% fetal bovine serum (FBS) and supplemented with calcium chloride at 70 µM final concentration.

Lymphocytes were cultured in RPMI-1640 media with 100 U/mL penicillin, 100 µg/mL streptomycin, 1 mM sodium pyruvate, 292 µg/mL L-glutamine, supplemented with 10% FBS or 10% heat inactivated human serum (HS). HaCaT cells were cultured at sub-confluency to avoid cell differentiation and used in assays at passage 60-70. Cells were plated at 2.5×103 cells/well in 96-well flat plate (Corning Costar) and cultured overnight to reach confluence. HaCaTs were washed once with PBS before treatment with 150 J microwave, liquid nitrogen (10 s), heat (42° C. preheated media) or with LPS+ IFN-γ (1 ng/mL+1000 U/mL). Cells were cultured for 24 h before supernatants were harvested.

For HPV-specific T cell lines, PBMCs were isolated from HLA-A2 individuals as previously described 11. PBMCs were seeded at 2-4×106 cells/well in 24-well culture plate and 10 µg/mL of 9 mer HLA-A2 restricted HPV16 epitope LLM (LLMGTLGIV) 12 was added, cells were cultured in 1 mL RPMI+10% HS. On day 3, cells were fed with RPMI+10% HS+IL-2 (200 IU/mL), and then fed again on day 7 or when needed. After day 10, HPV-specific T cells were harvested for cryopreservation before testing against HPV in ELISpot assays.

Monocyte derived dendritic cells (moDCs), CD14+ cells were positively isolated from PBMCs by magnetic separation using CD14 microbeads (Milentyi Biotec), according to manufacturer's protocol. Cells were washed and resuspended in RPMI+10% FBS+250 U/mL IL-4 and 500 U/mL GM-CSF. At day 3, cells were fed with RPMI+10% FBS+IL-4 and GM-CSF, and then harvested on day 5 for use in functional assays.

In vitro, microwave therapy of cell cultures was delivered through the base of the plastic culture dish and showed a linear dose response between the energy delivered and thermal induction (not shown). Utilising the equation E=m× c×θ (E=energy transferred, J; m=mass, kg; c=specific heat capacity, J/kg ° C.; θ=temperature change, ° C.), we calculated that in our system the 150 J Swift programme delivered 15.58 J (s.d. 0.921) through the plastic to the culture.

ELISpot, Flow Cytometry and qPCR

Keratinocytes were treated with microwave at various energy settings before removal of supernatant at various time points. MoDCs were treated overnight with keratinocyte supernatant, then washed twice before incubation with 10 µg/mL LLM peptide for 2 hours before a further wash.

Human IFN-γ ELISpot (Mabtech, Sweden) was undertaken as per manufacturer's protocol and as reported previously 11. 1×103 moDCs were plated with autologous HPV peptide-specific T cells at 1:25 ratio. Spot forming units (sfu) were enumerated with ELISpot 3.5 reader (AID, Germany).

MoDCs were treated with HaCaT supernatant and harvested at 24 hours for flow cytometric analysis of cell phenotype. Cells were stained with violet LIVE/DEAD stain (Invitrogen) for 30 min at 4° C., then washed with PBS+1% BSA and stained with antibodies PerCP-Cy5.5 anti-HLA-DR, FITC anti-CD80, FITC anti-CD86, PE anti-CD40, all purchased from BD, for 45 min at 4° C. Cells were washed then resuspended in PBS+1% BSA and analysed using the BD FACSAria and the FlowJo v10.0.08 analysis software.

The expression of chosen genes was validated with quantitative PCR, using the TaqMan gene expression assays for target genes: YWHAZ (HS03044281_g1), IRF1 (Hs00971960_m1), IRF4 (Hs00543439_CE) (Applied Biosystems, Life Technologies, Paisley, UK) in human skin treated as indicated. RNA extraction (RNeasy micro kit, Qiagen) and reverse transcription (NanoScript kit; Primer Design, Southampton, UK) were carried out accordingly to the manufacturer's protocol.

Results:

Treatment of Human Papilloma Virus Infection in Humans with Microwave Therapy

From January 2015 to September 2015 at the University of Southampton, we enrolled 32 patients with severe, treatment-refractory plantar warts. The diagnosis of plantar wart was confirmed by a podiatrist experienced in management of such lesions. A clinically significant wart was defined as >1 year duration, which had failed at least two previous treatments (salicylic acid, laser, cryotherapy, needling and surgical excision). In each patient, the most prominent plantar wart (most severely affected) was targeted for treatment (FIGS. 10A and 10B).

Figure 10C:
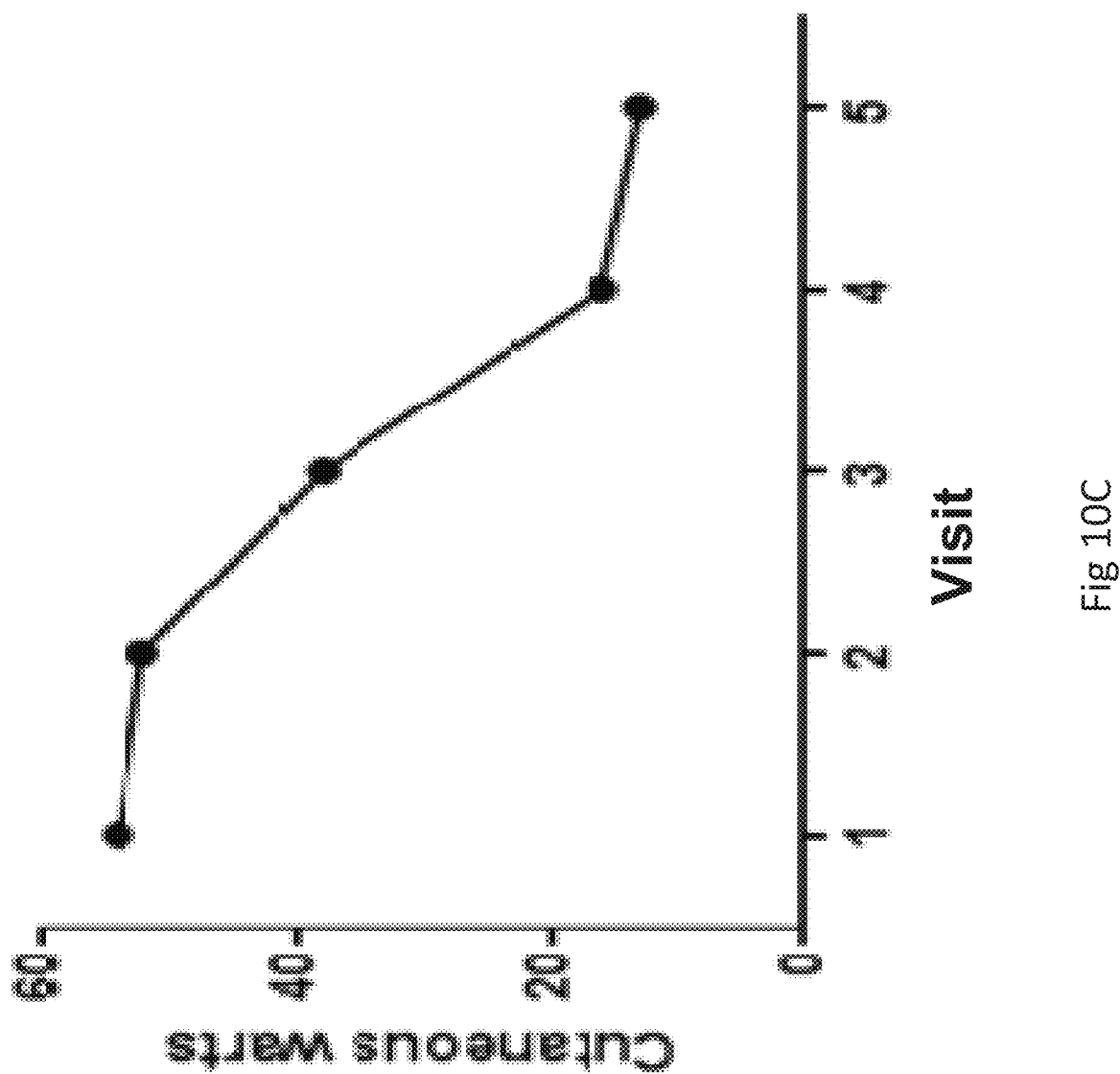
FIG. 10C: Intention to treat analysis of 32 patients with 54 HPV foot warts were treated by microwave therapy over 5 visits: baseline, 1 week, 1 month, 3 months, and 12 months. Resolved warts were enumerated.

At the end of the study period, of the 54 warts treated, 41 had resolved (75.9%), 9 remained unresolved (16.7%), 3 warts (n=2 patients) had withdrawn from the study (5.6%) and 1 patient (with 1 wart) was lost to follow up (1.9%). The mean number of days to resolution 79.49 days (sd 34.561; 15-151 days). 94% of resolving lesions had cleared after 3 treatments (FIG. 10C). No significant difference in resolution rates were observed between males and females (p=0.693) was observed.

Microwave Treatment of Human Skin

Human skin has not been previously treated with microwave therapy, therefore, we proceeded to undertake a full histological analysis. Skin removed during routine surgery was sectioned 1 hour after treatment ex vivo. Neither macroscopic, nor histological changes were noted with the lowest energy setting (5 J). At 50 J, mild macroscopic epidermal changes only were noted, and microscopically minor architectural changes, and slight elongation of keratinocytes were seen without evidence of dermal collagen sclerosis. At higher energies (100, 200 J) gross tissue contraction was visible macroscopically. Microscopic changes in the epidermis were prominent, showing spindled keratinocytes with linear nuclear architectural changes and sub-epidermal clefting (FIG. 11A).

Figure 11A:
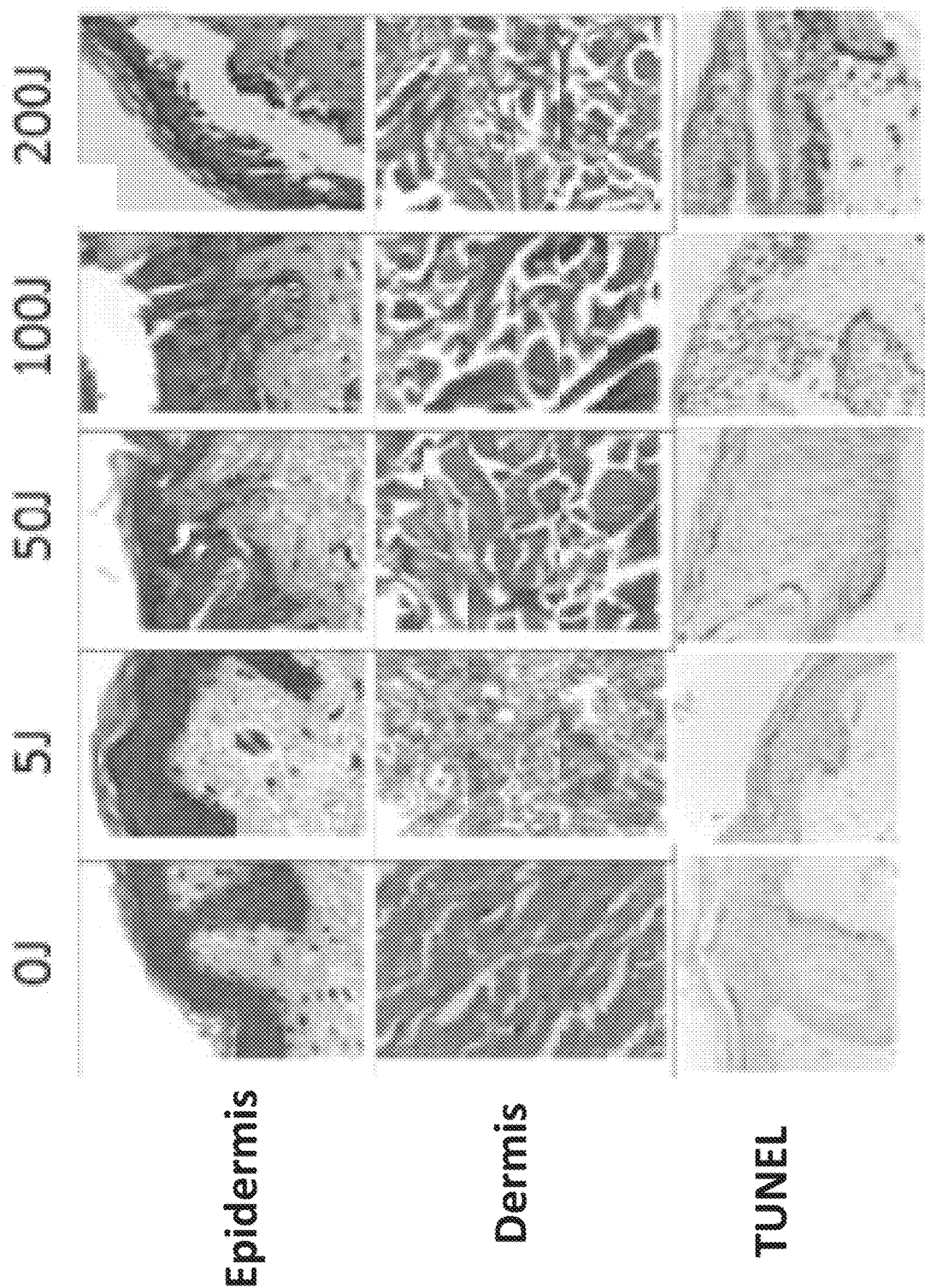
FIG. 11A: Histological analysis of human skin treated with microwave visualised at the epidermis/papillary dermis (top and bottom panels), or deep dermis (middle panels). Skin was subject to microwave therapy (0-200 J), before punch excision. Tissue was cultured for 1 hour before fixation and paraffin embedding. H&E or TUNEL staining. Original magnifications, ×20.

Dermal changes were prominent at energies of 100 J and above and showed a homogenous zone of papillary dermal collagen, thickened collagenous substances, accentuation of basophilic tinctorial staining of the dermal collagen with necrotic features (FIG. 11A). These features are similar to electrocautery artefacts and suggest the potential to induce scarring at >100 J. Histological analysis both at 16 h and 45 h showed similar changes (not shown).

Figure 11B:
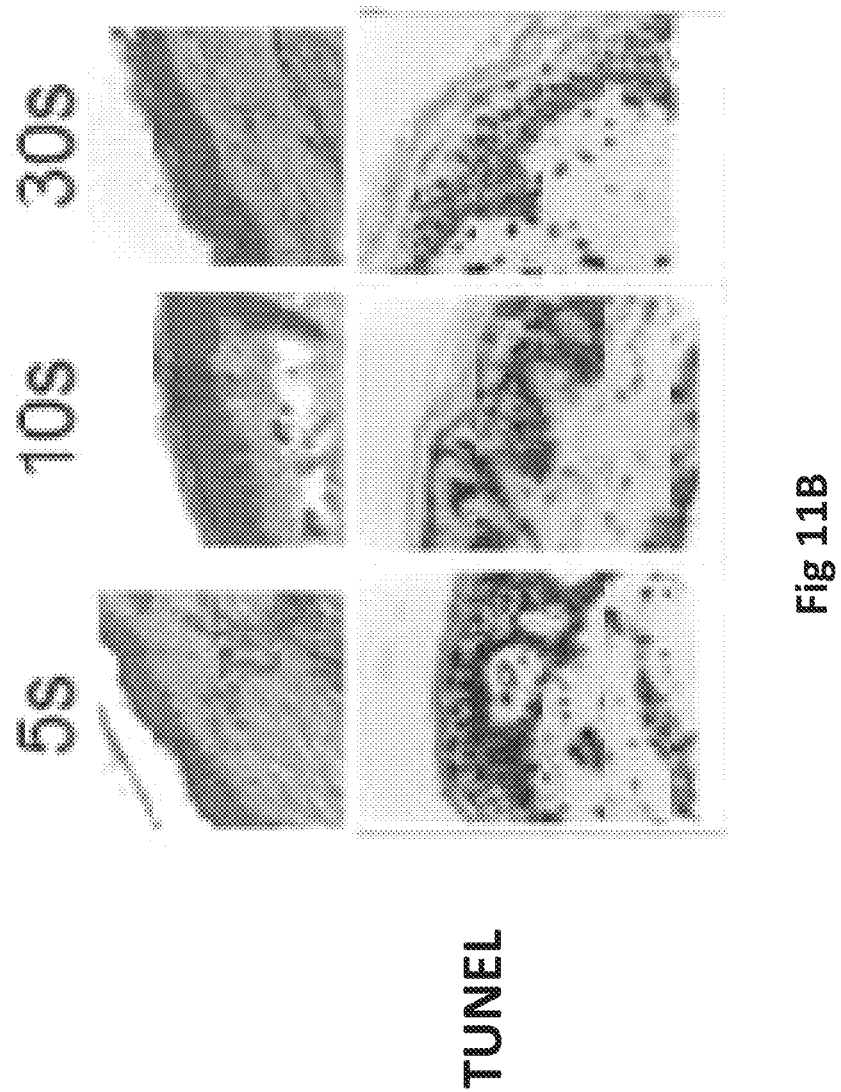
FIG. 11B: Histological analysis of human skin treated with microwave visualised at the epidermis/papillary dermis (upper panels), or deep dermis (lower panels). Skin was subject to various liquid nitrogen therapy for 5, 10, or 30 seconds, before punch excision. Tissue was cultured for 1 hour before fixation and paraffin embedding. H&E or TUNEL staining. Original magnifications, ×20.

In clinical practice, cryotherapy is delivered to the skin by cryospray, which is time-regulated by the operator. In contrast to microwave therapy, minimal epidermal or dermal architectural change was identified with cryotherapy at standard treatment duration times (5-30 s), but did show a dose dependent clumping of red blood cells in vessels (FIG. 11B).

Figure 11C:
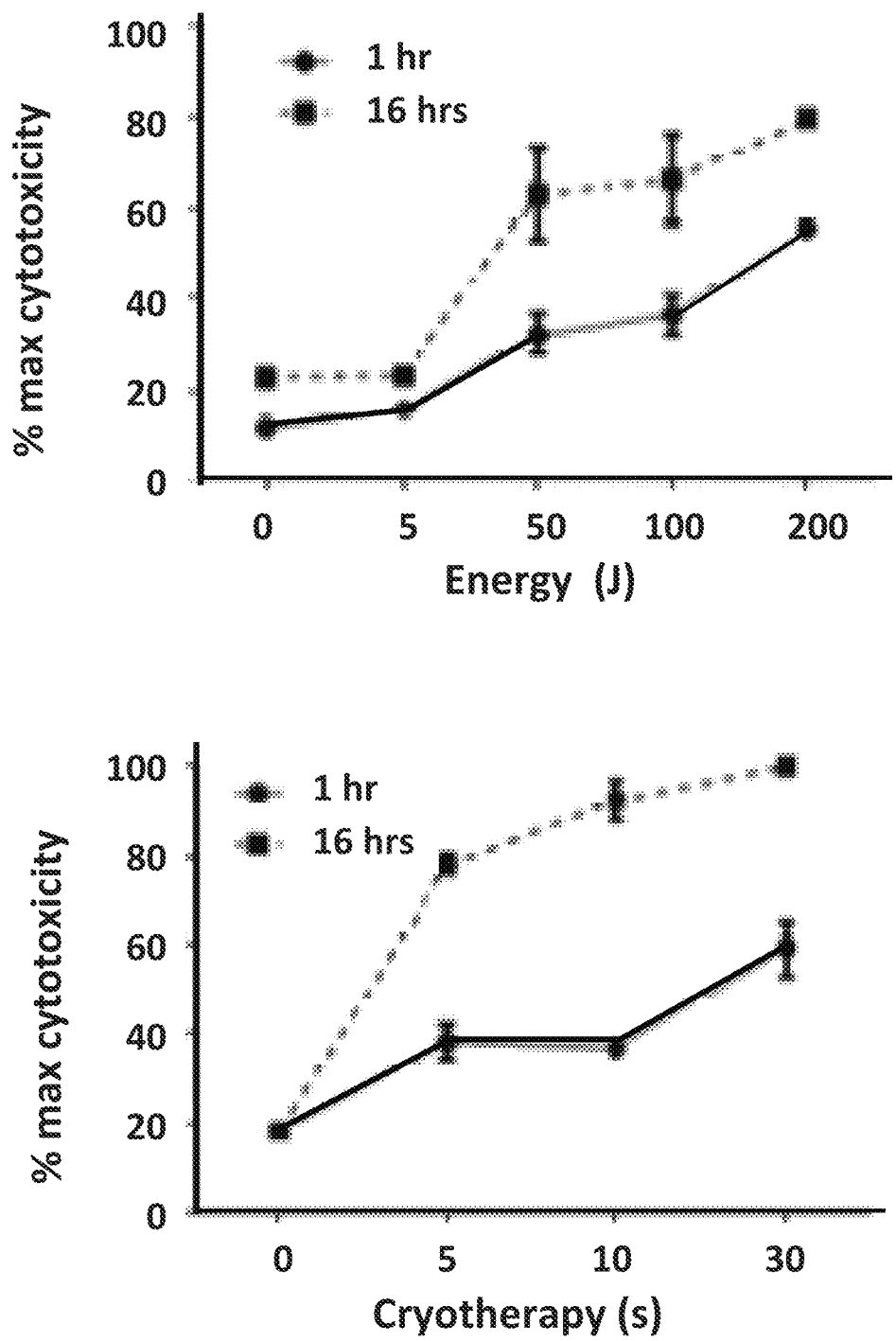
FIG. 11C: Following microwave therapy (top panel) or cryotherapy (bottom panel), skin samples (in triplicate) were excised and cultured in media for 1 or 16 hours before harvesting supernatant for measurement of lactate dehydrogenase (LDH) by ELISA.

Tissue release of LDH acts as a biomarker for cellular cytotoxicity and cytolysis. To examine the extent of cell death induced by microwave irradiation, human skin was treated with 0, 50, 100 or 200 J before punch excision of the treated area and incubation in medium for 1 hour or 16 hours. Measurement of LDH revealed a dose dependent induction of tissue cytotoxicity with increasing microwave energies (FIG. 11C). In line with the lack of histological evidence of cellular damage, at 5 J, cytotoxicity of microwave application was equivalent to control. Early cytotoxicity was not prominent at 50 J, but became more evident after 16 hours. Higher energy levels induced more prominent cytotoxic damage. In contrast to microwave therapy, liquid nitrogen treatment of skin induced cytotoxicity at the lowest dose both at 1 hour and 16 hours.

Terminal deoxynucleotidyl transferase dUTP nick end labelling (TUNEL) identifies cells in the late stage of apoptosis. Analysis at 0, 5, 50, 100 and 200 J identified increased cellular apoptosis in the epidermis above 100 J (FIG. 11A). In contrast, cryotherapy with a liquid nitrogen spray applicator directly to the skin as used in clinical practice, even at a very short treatment time (5 s) induced significant epidermal and dermal DNA fragmentation (FIG. 11B).

Figure 11D:
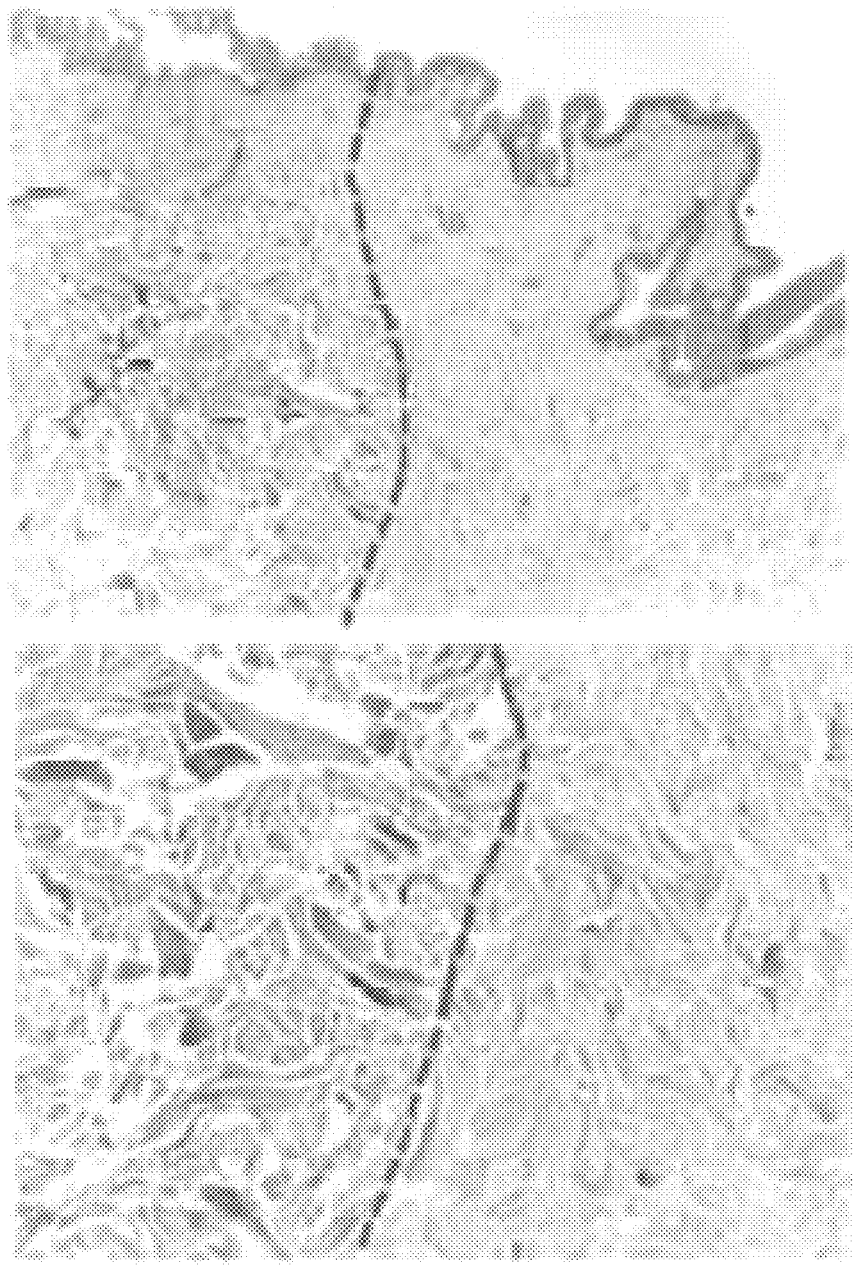
FIG. 11D: Skin was subject to microwave therapy (150 J), before punch excision at the margin of the treated zone. Tissue was cultured for 1 hour before fixation and paraffin embedding. H&E stain. Original magnifications, ×10.
Figure 11E:
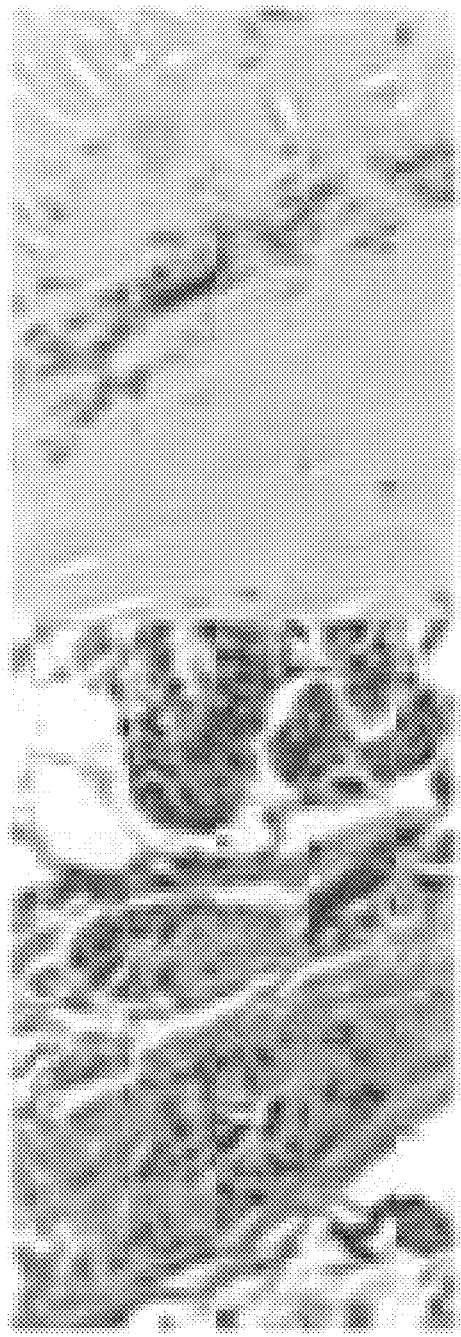
FIG. 11E: Skin was subject to microwave therapy (150 J), before punch excision. Tissue was cultured for 1 hour before fixation and paraffin embedding. H&E stain showing deep dermis. Original magnifications, ×100. Representative of 3 independent experiments.

The physics of microwave therapy suggests a tight boundary between treated and untreated tissue with minimal spreading of the treated field. This was borne out histologically by a clear demarcation between treated areas extending vertically from the epidermis through the dermis (FIG. 11D). Examination of the dermis showed that microwave therapy modified skin adnexae inducing linear nuclear architectural changes in glandular apparatus, microthrombi, fragmented fibroblasts and endothelial cells (FIG. 11E).

Microwave Induction of Immune Responses in Skin

Figure 12A:
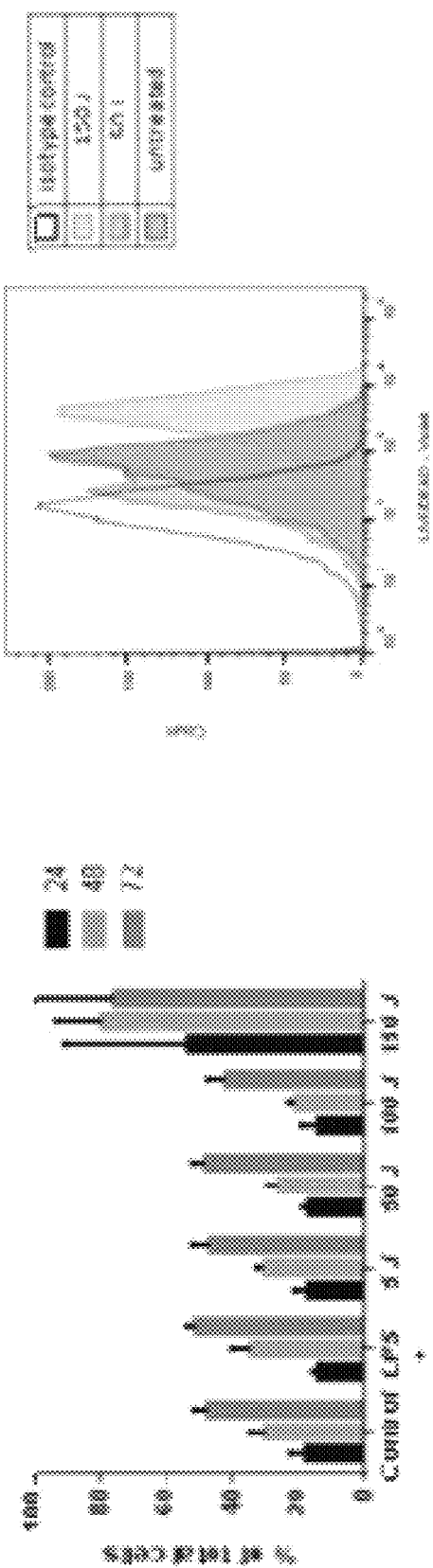
FIG. 12A: Left. Flow cytometric analysis of viable keratinocytes (% of total cells) indicated by negative staining with the amine reactive viability dye LIVE/DEAD after control, microwave (5-150 J), or LPS/IFNg treatment. Keratinocytes were treated, then kept in culture for 24, 48 or 72 hours before analysis. Right. Flow cytometric analysis of keratinocyte viability after microwave therapy or control depicted as a histogram. X-axis: MFI LIVE/DEAD stain; y-axis: cell count.
Figure 12B:
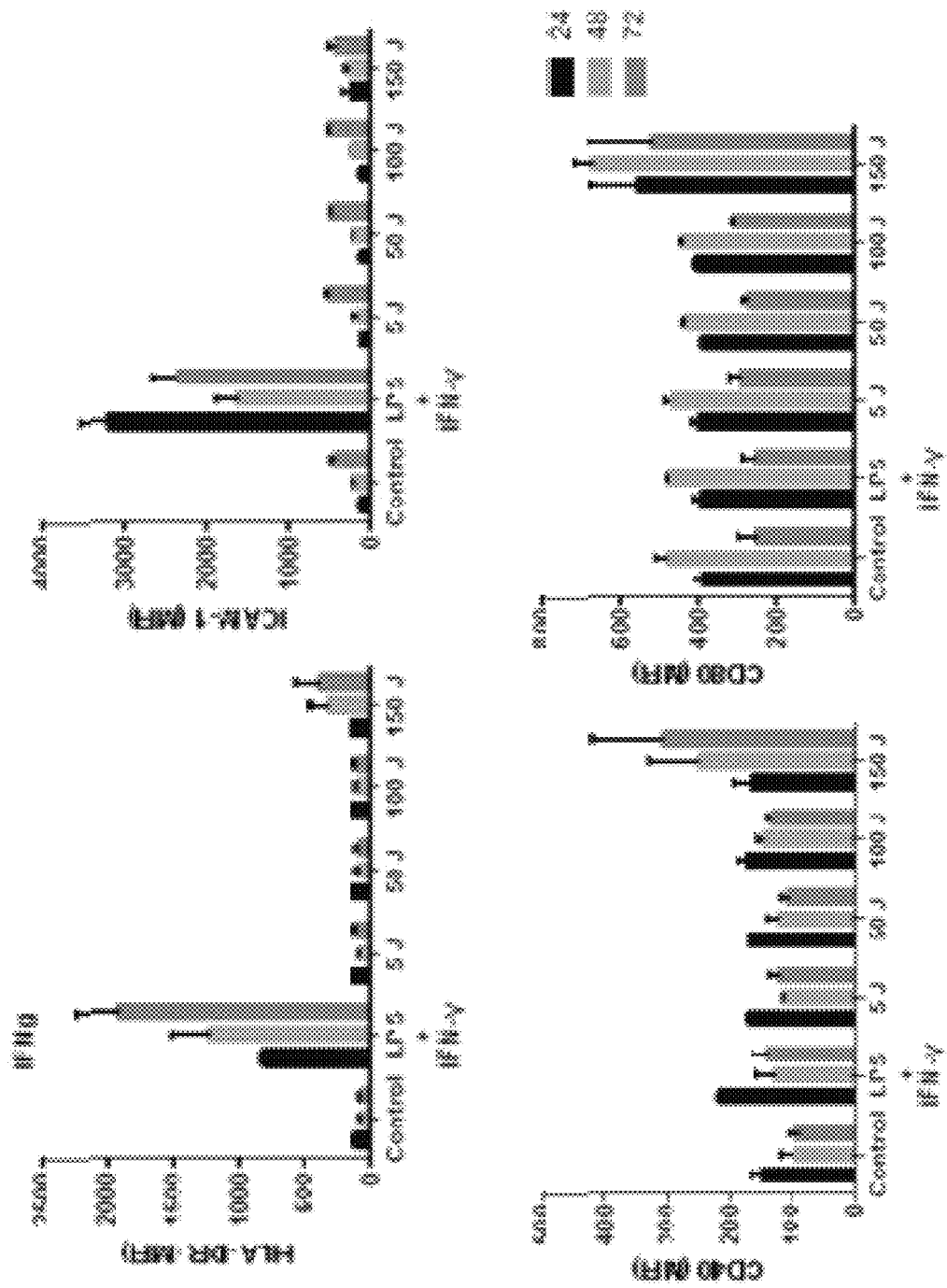
FIG. 12B: Flow cytometric analysis of HLA-DR, ICAM-1, CD40 or CD80 expression on viable keratinocytes. Keratinocytes were treated with microwave therapy (5-150 J), LPS/IFNg, or nil (control), rested in culture for 24, 48 or 72 hours, before analysis of the viable population.
Figure 12C:
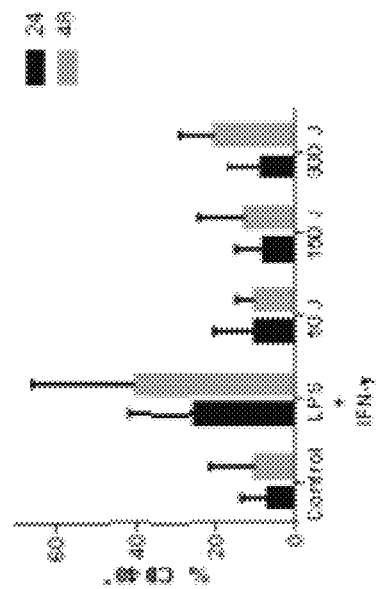
FIG. 12C: Flow cytometric analysis of CD86, CD80, and CD40 expression on viable monocyte derived dendritic cells (moDCs). Keratinocytes were treated with microwave therapy (5-150 J), LPS/IFNg, or nil (control), rested in culture for 8 hours then washed. They were left in culture for the remaining time until 24 or 48 hours, before transfer of supernatant onto moDCs. MoDCs were incubated for 24 hours before harvesting for analysis. Data representative of 3 independent experiments. Mean+SD.
Figure 12C:
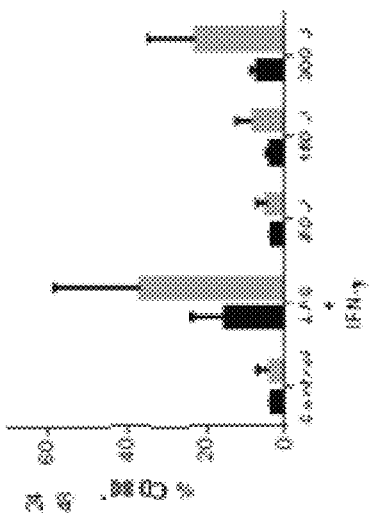
Figure 12C:
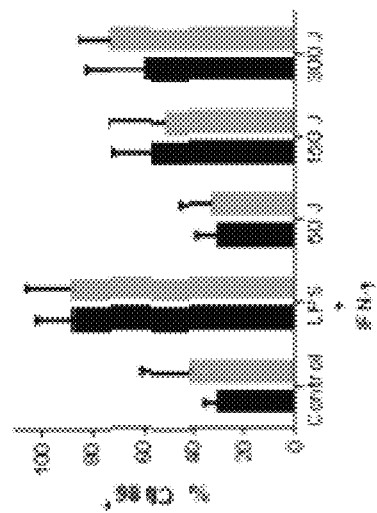

We first examined the response of keratinocytes to microwave therapy in vitro. Keratinocyte apoptosis was induced by microwave therapies above 100 J in vitro (FIG. 12A). Only above the apoptotic threshold were surface phenotypic changes of cellular activation noted in viable cells with increased expression of HLA-DR, CD40 and CD80 (FIG. 12B). Next, we utilised a model of skin cross talk of keratinocyte signalling to dermal dendritic cells. Keratinocytes were treated with microwave therapy as above, and washed after 8 hours to remove dead or apoptotic cells. Treated keratinocytes were then incubated for a further 16 hours before supernatant collection to prime monocyte derived dendritic cells (moDCs) which had not been directly exposed to microwave therapy. This showed a potent induction of moDC activation with increased expression of CD86, CD80 and to a lesser extent CD40 (FIG. 12C).

Figure 13A:
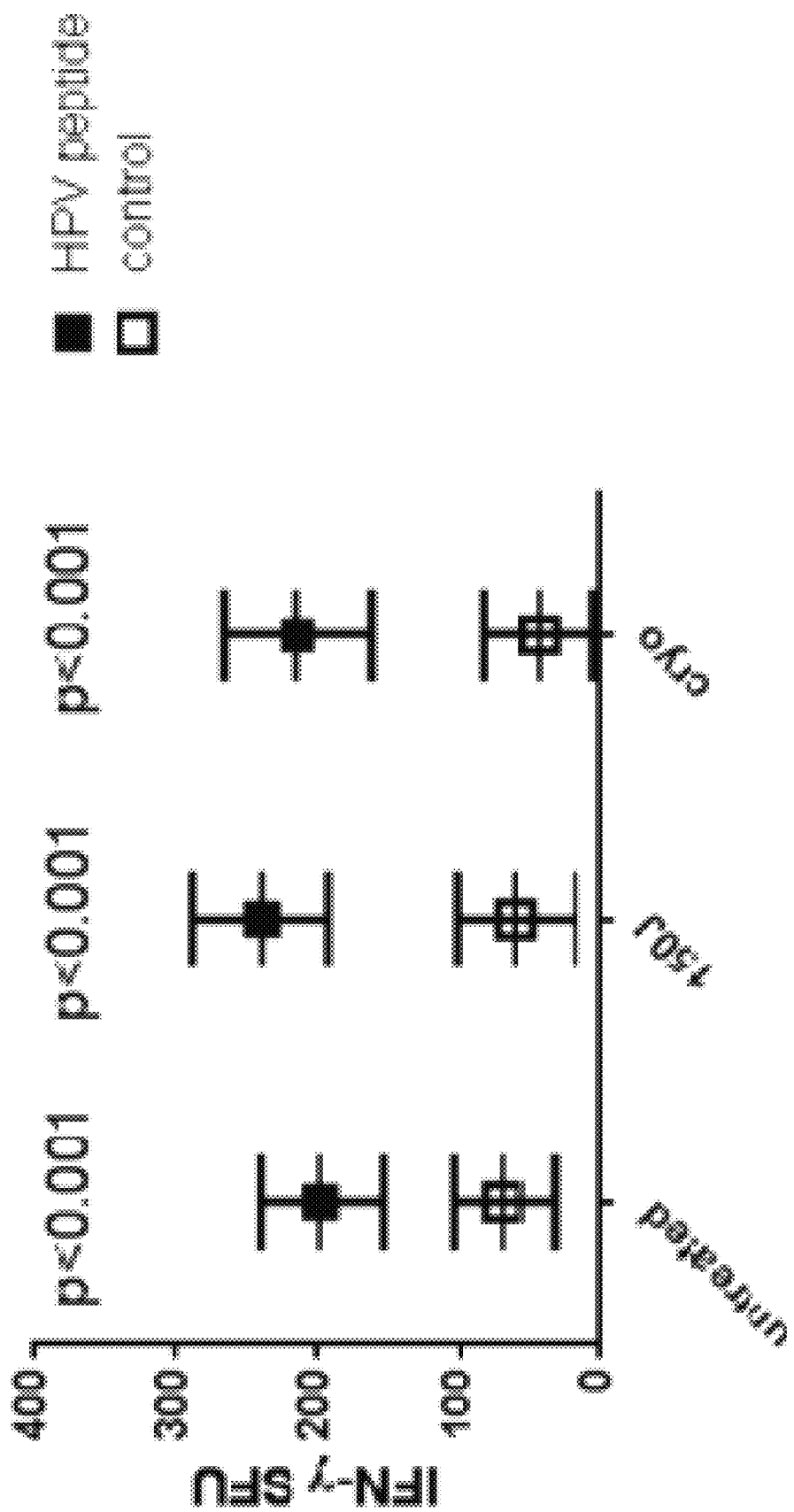
FIG. 13A: ELISpot assay of IFN-γ production by HPV-specific CD8+ cells following co-culture with HPV peptide pulsed moDCs primed by supernatant from untreated, microwave treated (150 J) or cryotherapy (cryo) treated keratinocytes. moDCs were primed with supernatant for 24 hours prior to pulsing with control or HPV peptide for 2 hours. Pulsed moDCs were then cocultured with an HLA-matched CD8+ HPV-specific T cell line before assay with IFN-γ ELISpot. Statistical significance determined using the Holm-Sidak method, with alpha=5%. Data representative of 3 independent experiments. Mean+SD.
Figure 13B:
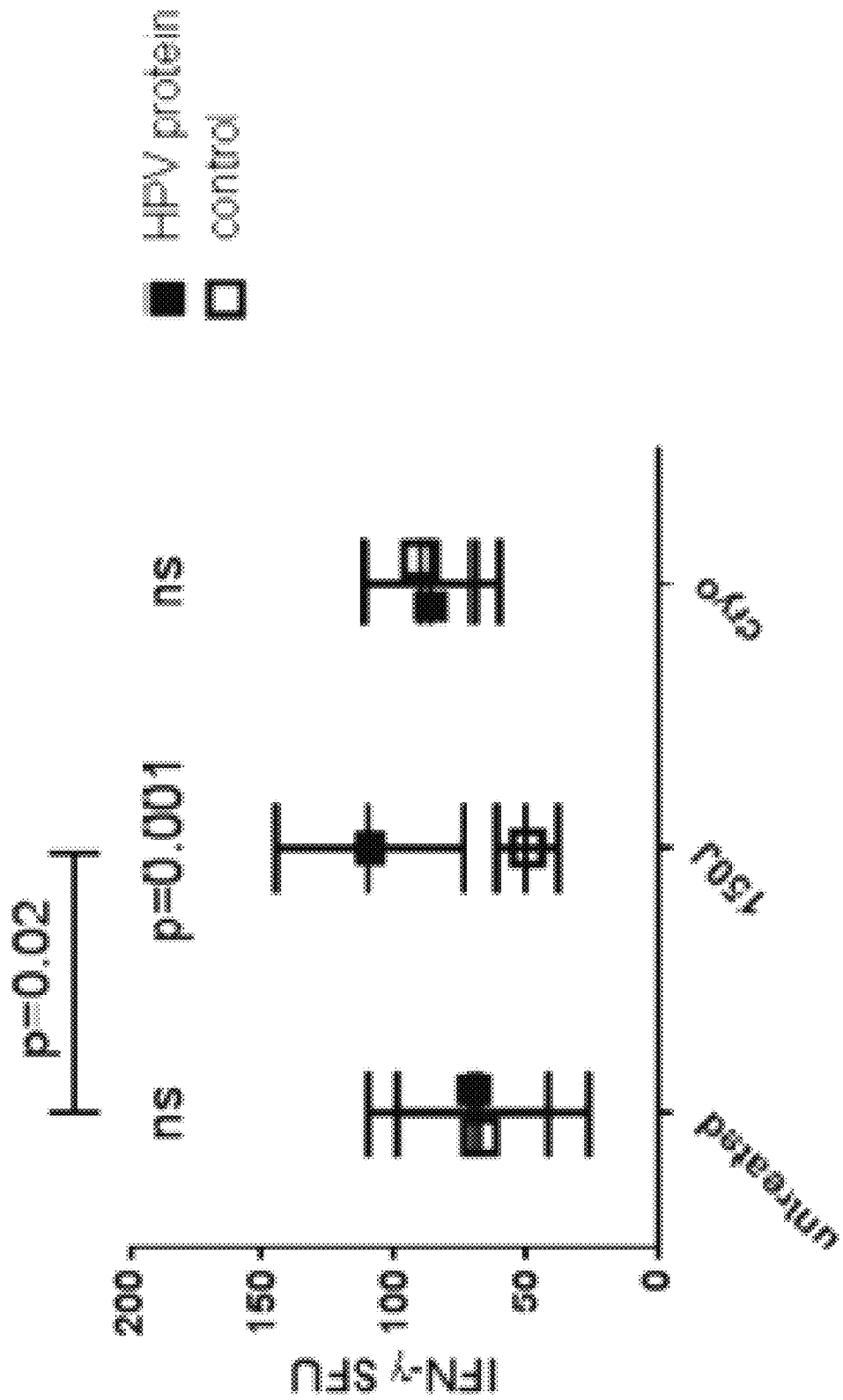
FIG. 13B: ELISpot assay of IFN-γ production by HPV-specific CD8+ cells following co-culture with HPV E16 protein pulsed moDCs primed by supernatant from untreated, microwave treated (150 J) or cryotherapy (cryo) treated keratinocytes. moDCs were primed with supernatant for 24 hours prior to pulsing with control or HPV peptide for 2 hours. Pulsed moDCs were then co-cultured with an HLA-matched CD8+ HPV-specific T cell line before assay with IFN-γ ELISpot. Statistical significance determined using the Holm-Sidak method, with alpha=5%. Data representative of 3 independent experiments. Mean+SD.
Figure 13D:
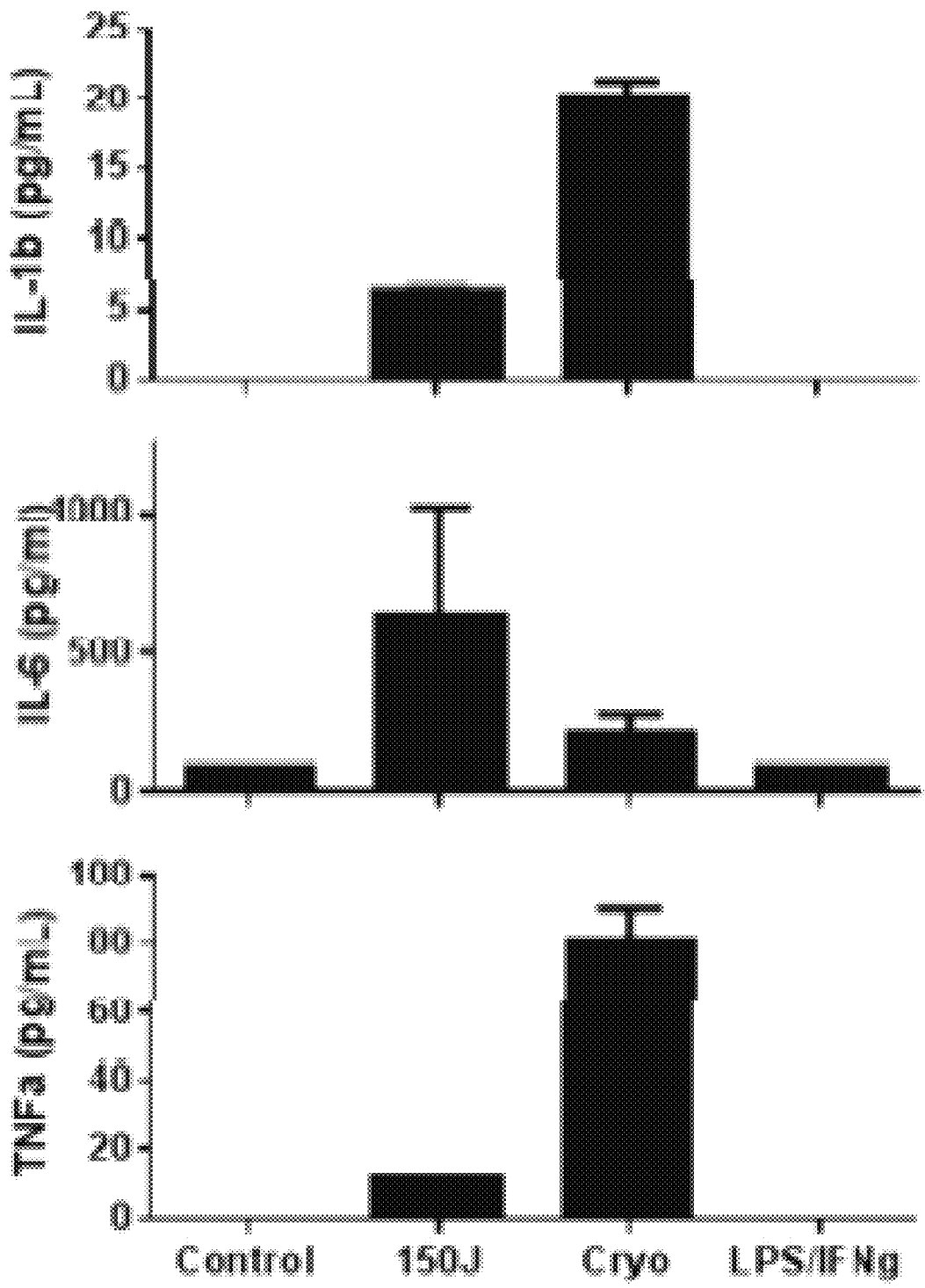
FIG. 13D: ELISA of IL-6, TNFα, IL-1β production by primary human keratinocytes 24 h after treatment with microwave therapy (150 J), LPS/IFNg, cryotherapy or nil (untreated).
Figure 13E:
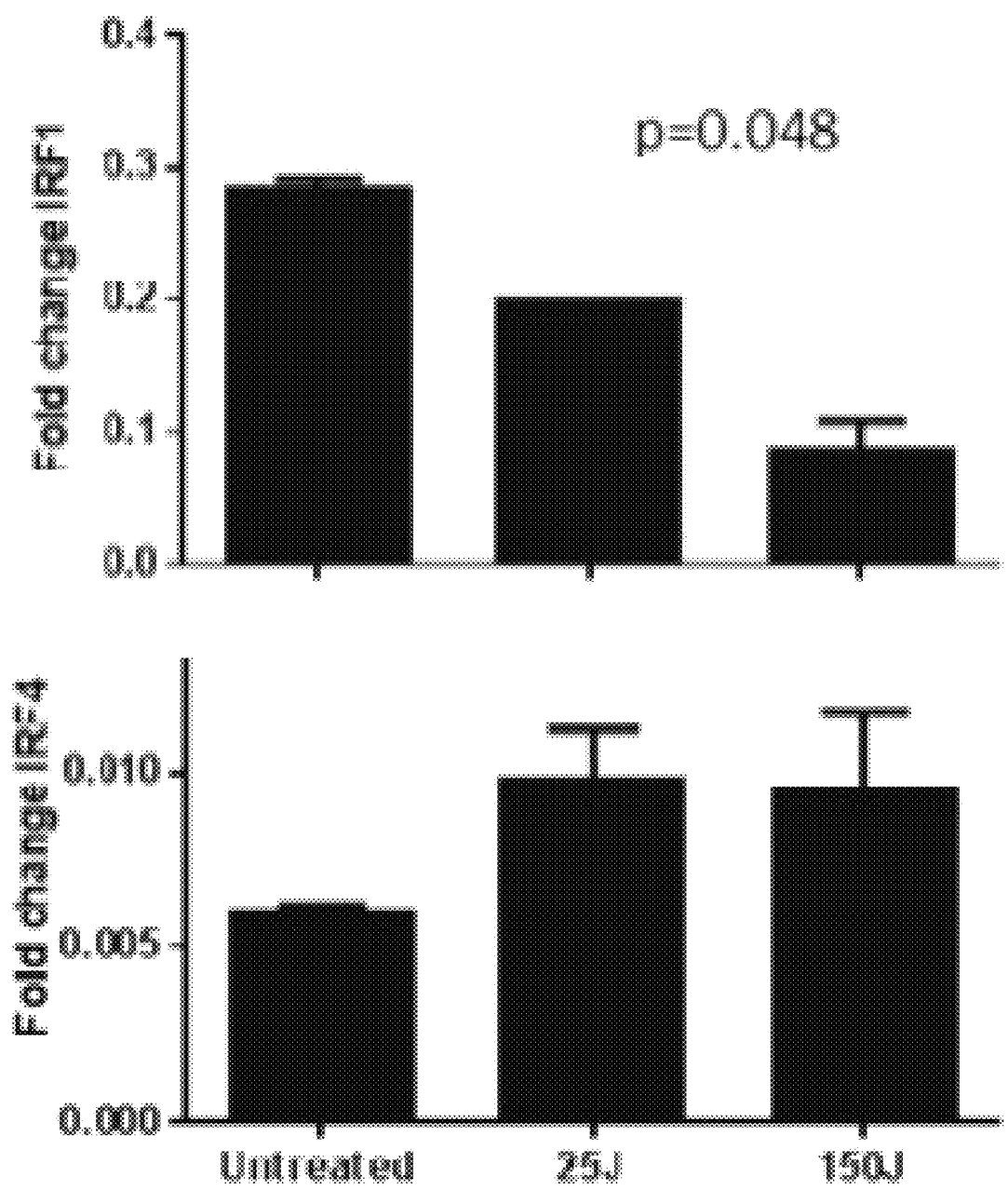
FIG. 13E: Expression changes of IRF1 and IRF4 in human skin with microwave therapy (25 J and 150 J) by qPCR.

We next set out to test the functional outcome on skin dendritic cells following microwave treatment of keratinocytes. Keratinocytes were untreated, microwave, or cryotherapy treated before supernatant harvesting. Supernatant primed DCs were pulsed with a 9 amino acid HLA-A2 epitope (LLM) from human papilloma virus (HPV) E16 protein and cultured with an autologous HPVspecific CD8+ T cell line. As expected, in all conditions, the DCs efficiently presented HPV peptide to CD8+ T cells inducing IFN-γγ (FIG. 13A). However, dendritic cell presentation of HPV virus is dependent upon cross-presentation to the MHC class I pathway. Therefore we also tested the ability of untreated, microwave treated or cryotherapy KC-primed DCs to present human papilloma virus (HPV) E16 protein to an HLA matched HPV-specific CD8+ T cell line. Strikingly, only microwave treated KCs were able to prime DCs to enhance cross-presentation (FIG. 13B). To explore the potential mechanism of keratinocyte response to microwave therapy we confirmed up regulation of HSP-70 in response to microwave therapy of keratinocytes (FIG. 13C) and showed significant IL-6 induction in keratinocytes above that seen in cryotherapy treated cells (FIG. 13D). IRF1 and IRF4 are key regulators of dendritic cell activation and we confirmed that microwave therapy induced down regulation of IRF1 and up-regulation of IRF4 (FIG. 13E).

DISCUSSION

This is the first study to investigate the potential efficacy of locally delivered microwaves in the treatment of cutaneous viral warts in vivo. We report a complete resolution rate of 75.9% recalcitrant plantar warts (average lesion duration of over 5 years). This compares very well with previous reports of plantar wart resolution for salicylic acid and or cryotherapy (23-33%)[13]. Whilst this study was a pilot phase, and did not include a control untreated arm, we believe the treatment effect to be significant.

For all novel therapies, adverse events are critical. In this study we did not identify a strong signal for adverse events with microwave therapy of cutaneous warts. As with current physical treatments for warts discomfort is expected for the patient. During the study patients typically reported that for a typical 5 second treatment that they endured moderate discomfort for approximately 2 seconds, which immediately diminished after the treatment had completed. In addition, it was commonly noted that discomfort was less with subsequent treatments. One male patient, withdrew from the study after one treatment, citing the pain of treatment as the reason. In the study design phase, preoperative use of topical anaesthetic cream was tested, but appeared to do little to mitigate the pain (unpublished data) and it was felt that the pain of local anaesthetic injection would exceed that normally experienced during a microwave treatment. Following microwave therapy, patients did not require dressings or special advice as microwave therapy utilised in this study did not cause a wound or ulcer in the skin, allowing the patient continue normal activity. The short microwave treatment time (5 s) offers a significant clinical advantage over current wart therapies such as cryotherapy and electrosurgery. Within 5 s, microwaves penetrate to a depth of over 3.5 mm at the energy levels adopted for the study[14]—possibly a greater depth than can be attained by cryosurgery or laser energy devices. Moreover, as microwaves travel in straight lines energy is deposited in alignment the device tip with little collateral spread, meaning minimal damage to surrounding tissue, as observed in this study. Microwaves induce dielectric heating. When water, as a polar molecule, is exposed to microwave energy, the molecule is excited and rotates attempting to align with the alternating electromagnetic field. At microwave frequencies the molecule is unable to align fully with the continuously shifting field resulting in heat generation. Within tissues, this acts to rapidly elevate temperatures. This process rapidly changes cellular heat because it does not depend on tissue conduction. Microwave treatment produces no vapour or smoke unlike ablative lasers and electro-surgery, eliminating the need for air extraction systems due to the risk of spreading viral particles within the plume[15].

Although, microwave therapy has been considered a tissue ablation tool, we saw minimal skin damage after treatment with 50 J, yet apparent good clinical response.

Therefore we investigated whether there was evidence to support an induction of immunity by microwave therapy. The critical nature of CD8+ T cell immunity for host defense against HPV skin infection is well established and supported by the observation of increased prevalence of infection in immunosuppressed organ transplant recipients[16], and that induction of protection from HPV vaccines is mediated by CD8+ T cells[17]. We show here, that microwave therapy of skin induces keratinocyte activation and cell death through apoptosis. However, at sub-apoptotic doses, microwave primed keratinocytes are able to signal to dendritic cells and enhance cross-presentation of HPV antigens to CD8+ lymphocytes which offers a potential explanation for the observed response rate in our clinical study. In vitro evidence suggests that this is likely to be mediated by cross-talk between microwave treated skin keratinocytes and dendritic cells, with resultant enhanced cross-presentation of HPV protein to CD8+ T cells. Microwave therapy also induced enhanced IL-6 synthesis from keratinocytes.

IL-6, is a pro-inflammatory mediator, important in antiviral immunity which has been recently shown to induce rapid effector function in CD8+ cells[18]. Thus, IL-6 up-regulation may provide an important additional mechanism for microwave anti-viral immunity. IRFs have been shown to be central to the regulation of immune responses[19-21]. IRF4 is essential for differentiation of cytotoxic CD8+ T cells[22][23], but up-regulation in dendritic cells has also been shown to enhance CD4+ differentiation, thereby potentially enhancing both CD8+ immunity and T cell help following microwave treatment. IRF1 expression has been previously reported to be modulated by HPV infection, but different models have shown opposite outcomes[24,25]. We show down-regulation of IRF1 in human skin in association with a microwave therapy which supports the proposal of IRF-1 as a therapeutic target in HPV infection[25].

This study is the first of its kind studying microwaves in the treatment of plantar warts in vivo. However, the authors acknowledge the limitations of the uncontrolled, non-randomised design. Despite the promising results shown here, studies with larger sample sizes are needed to assess the efficacy of this treatment and for infrequent but serious adverse events.

It will be understood that embodiments of the present invention have been described above purely by way of example, and modifications of detail can be made within the scope of the invention.

Each feature disclosed in the description, and (where appropriate) the claims and drawings may be provided independently or in any appropriate combination.

REFERENCES

1. Cockayne S, Hewitt C, Hicks K, et al. Cryotherapy versus salicylic acid for the treatment of plantar warts (verrucae): a randomised controlled trial. BMJ 2011; 342:d3271.
2. Stern P L. Immune control of human papillomavirus (HPV) associated anogenital disease and potential for vaccination. Journal of clinical virology: the official publication of the Pan American Society for Clinical Virology 2005; 32 Suppl 1:S72-81.
3. Soong R S, Song L, Trieu J, et al. Toll-like receptor agonist imiquimod facilitates antigenspecific CD8+ T-cell accumulation in the genital tract leading to tumor control through IFNgamma. Clin Cancer Res 2014; 20:5456-67.
4. Edwards L, Ferenczy A, Eron L, et al. Self-administered topical 5% imiquimod cream for external anogenital warts. HPV Study Group. Human PapillomaVirus. Arch Dermatol 1998; 134:25-30.
5. Bristow I, Walker N. Pulsed Dye laser for the treatment of plantar warts—two case studies. Foot 1997; 7:229-30.
6. Kimura U, Takeuchi K, Kinoshita A, Takamori K, Suga Y. Long-pulsed 1064-nm neodymium:yttrium-aluminum-garnet laser treatment for refractory warts on hands and feet. The Journal of Dermatology 2014; 41:252-7.
7. Park H, Choi W. Pulsed dye laser treatment for viral warts: A study of 120 patients. Journal of Dermatology 2008; 35:491-8.
8. Tosti A, Piraccini B M. Warts of the Nail Unit: Surgical and Nonsurgical Approaches. Dermatol Surg 2001; 27:235-9.
9. Sterling J C, Gibbs S, Haque Hussain S S, Mohd Mustapa M F, Handfield-Jones S E. British Association of Dermatologists' guidelines for the management of cutaneous warts 2014. Br J Dermatol 2014; 171:696-712.
10. Lloyd D M, Lau K N, Welsh F, et al. International multicentre prospective study on microwave ablation of liver tumours: preliminary results. HPB: the official journal of the International Hepato Pancreato Biliary Association 2011; 13:579-85.
11. Polak M E, Thirdborough S M, Ung C Y, et al. Distinct molecular signature of human skin Langerhans cells denotes critical differences in cutaneous dendritic cell immune regulation. J Invest Dermatol 2014; 134:695-703.
12. Ressing M E, de Jong J H, Brandt R M, et al. Differential binding of viral peptides to HLA-A2 alleles. Implications for human papillomavirus type 16 E7 peptide-based vaccination against cervical carcinoma. European journal of immunology 1999; 29:1292-303.
13. Bruggink S C, Gussekloo J, Berger M Y, et al. Cryotherapy with liquid nitrogen versus topical salicylic acid application for cutaneous warts in primary care: randomized controlled trial. CMAJ 2010; 182:1624-30.
14. Emblation Medical Limited. Swift applicator instructions for use. Alloa, Scotland 2012.
15. Karsai S, Daschlein G. "Smoking guns": Hazards generated by laser and electrocautery smoke. J Dtsch Dermatol Ges 2012; 10:633-6.
16. Tan H H, Goh C L. Viral infections affecting the skin in organ transplant recipients: epidemiology and current management strategies. Am J Clin Dermatol 2006; 7:13-29.
17. de Jong A, O'Neill T, Khan A Y, et al. Enhancement of human papillomavirus (HPV) type 16 E6 and E7-specific T-cell immunity in healthy volunteers through vaccination with TA-CIN, an HPV16 L2E7E6 fusion protein vaccine. Vaccine 2002; 20:3456-64.
18. Bottcher J P, Schanz O, Garbers C, et al. IL-6 trans-signaling-dependent rapid development of cytotoxic CD8+ T cell function. Cell reports 2014; 8:1318-27.
19. Schlitzer A, McGovern N, Teo P, et al. IRF4 transcription factor-dependent CD11b+ dendritic cells in human and mouse control mucosal IL-17 cytokine responses. Immunity 2013; 38:970-83.
20. Vander Lugt B, Khan A A, Hackney J A, et al. Transcriptional programming of dendritic cells for enhanced MHC class II antigen presentation. Nat Immunol 2013.
21. Tussiwand R, Lee W L, Murphy T L, et al. Compensatory dendritic cell development mediated by BATF-IRF interactions. Nature 2012; 490:502-7.

22. Huber M, Lohoff M. IRF4 at the crossroads of effector T-cell fate decision. European journal of immunology 2014; 44:1886-95.
23. Raczkowski F, Ritter J, Heesch K, et al. The transcription factor Interferon Regulatory Factor 4 is required for the generation of protective effector CD8+ T cells. Proc Natl Acad Sci USA 2013; 110:15019-24.
24. Park J S, Kim E J, Kwon H J, Hwang E S, Namkoong S E, Um S J. Inactivation of interferon regulatory factor-1 tumor suppressor protein by HPV E7 oncoprotein. Implication for the E7-mediated immune evasion mechanism in cervical carcinogenesis. J Biol Chem 2000; 275:6764-9.
25. Muto V, Stellacci E, Lamberti A G, et al. Human papillomavirus type 16 E5 protein induces expression of beta interferon through interferon regulatory factor 1 in human keratinocytes. Journal of virology 2011; 85:5070-80.

The invention claimed is:

1. A method of stimulating a localized immune response, said method comprising:
   administering a therapeutically effective amount or dose of microwave energy to tissue of a subject in which a localized immune response is to be stimulated, wherein the administering the therapeutically effective amount or dose of microwave energy to the tissue comprises:
   measuring or receiving a dielectric constant of tissue;
   identifying that the tissue has a condition associated with HPV or an HPV infection based on the measured or received dielectric constant of the tissue;
   using a delivery system to administer the therapeutically effective amount or dose of microwave energy via a microwave applicator to the tissue of the subject; and
   repeatedly applying, by the microwave applicator, the microwave energy
   in a pulsed manner thus providing repeated rounds of localized hyperthermia and repeated localized stimulation of the immune response to the tissue,
   wherein the tissue has a lesion, and wherein the administering of the therapeutically effective amount or dose of microwave energy to the tissue comprises electrically matching the microwave applicator to the tissue, based on the tissue having a lower dielectric constant than a dielectric constant that said tissue would have if said tissue did not have said lesion, such that the microwave applicator is better matched to the tissue that has said lesion than the microwave applicator would have been if said tissue did not have said lesion.

2. The method of claim 1, and wherein the microwave energy is selected such as to expose antigenic sites stimulating the localized immune response at the lesion, and wherein the lesion is a recalcitrant HPV infection that has failed at least two other treatments selected from the group consisting of a salicylic acid-based treatment, a laser treatment, cryotherapy, needling, and surgical excision.

3. The method of claim 2, wherein the recalcitrant HPV infection has persisted for at least one year, and wherein the microwave energy is administered at one or more doses of 1 W to 10 W for 1s to 5s.

4. The method of claim 1, wherein the microwave energy has a frequency
   between about 500 MHz and about 200 GHz;
   between about 900 MHz and about 100 GHz; or
   between about 5 GHz to about 15 GHz.

5. The method of claim 1, wherein the microwave energy has a frequency of about 8 GHz.

6. The method of claim 1, wherein the microwave energy is applied at an energy of between about 1J and about 50J.

7. The method of claim 1, wherein the microwave energy is applied at 10W for 5s.

8. The method of claim 1, wherein the therapeutically effective amount or dose of microwave energy produces, induces, elevates an immune response and/or levels of heat shock factor (HSF) to stimulate production of a heat shock protein, in or near the tissue.

9. The method of claim 8, wherein the heat shock protein is selected from the group consisting of HSP90, HSP72, HSP70, HSP65, HSP60, HSP27, HSP16, and any another heat shock protein.

10. The method of claim 9, wherein the microwave energy promotes an association between the elevated heat shock protein and the tissue so as to elicit the immune response against an infection causing the lesion.

11. The method of claim 8, wherein the immune response is a cell and/or cytokine based immune response.

12. The method of claim 1, wherein the microwave energy induces the immune response, cauterises, coagulates, shrinks, blocks, ablates, damages, irritates, inflames, or otherwise interferes with the normal operation of capillaries supplying blood to the lesion.

13. The method of claim 1, wherein the therapeutically effective amount or dose of microwave energy is administered to tissue susceptible to the formation of an HPV lesion, wherein the microwave energy induces the immune response or causes the denaturing of viral particles within the HPV lesion thus exposing antigenic sites further stimulating an immune response.

* * * * *